(12) United States Patent
Levine et al.

(10) Patent No.: US 11,457,948 B2
(45) Date of Patent: Oct. 4, 2022

(54) BENDABLE TROCARS HAVING BLUNT TIPS AND CONNECTORS FOR ADVANCING WOUND DRAIN CATHETERS THROUGH TISSUE

(71) Applicant: Ethicon, Inc., Somerville, NJ (US)

(72) Inventors: Serge Levine, Skillman, NJ (US); Jianxin Guo, Livingston, NJ (US); Michael McErlean, Downingtown, PA (US); Jonathan Addeo Syby, Manasquan, NJ (US)

(73) Assignee: Ethicon, Inc., Raritan, NJ (US)

( * ) Notice: Subject to any disclaimer, the term of this patent is extended or adjusted under 35 U.S.C. 154(b) by 590 days.

(21) Appl. No.: 16/277,192

(22) Filed: Feb. 15, 2019

(65) Prior Publication Data

US 2020/0261114 A1   Aug. 20, 2020

(51) Int. Cl.
*A61B 17/34* (2006.01)
*A61M 1/00* (2006.01)
(Continued)

(52) U.S. Cl.
CPC ....... *A61B 17/3417* (2013.01); *A61M 1/0023* (2013.01); *A61M 1/90* (2021.05);
(Continued)

(58) Field of Classification Search
CPC ............ A61B 17/3415; A61B 17/3417; A61B 2017/320056; A61B 2017/3456;
(Continued)

(56) References Cited

U.S. PATENT DOCUMENTS 1,313,461 A * 8/1919 Brown .................. D04B 17/04
66/117
4,359,053 A 11/1982 Benjamin
(Continued)

FOREIGN PATENT DOCUMENTS

EP 0370733 5/1990
EP 1800607 6/2007
(Continued)

OTHER PUBLICATIONS

International Search Report issued in corresponding International Application No. PCT/IB2020/051072, dated Apr. 20, 2020, 6 pages.

*Primary Examiner* — Adam Marcetich

(57) ABSTRACT

A trocar includes a shaft having a leading section, a trailing section, a reduced diameter midsection located between the leading and trailing sections, and a longitudinal axis extending along the length of the shaft. The leading section of the shaft has a tapered region that terminates at a blunt tip. The trailing section of the shaft has a connector located at the trailing end thereof. The leading and trailing sections of the shaft having a first diameter and the reduced diameter midsection of the shaft has a second diameter that is smaller than the first diameter for enabling the shaft to be bent at the reduced diameter midsection. A flexible wound drain catheter having a first end is secured to the connector at the trailing end of the trailing section of the shaft. The flexible wound drain catheter has an outer diameter that matches the first diameter of the leading and trailing sections of the shaft.

19 Claims, 24 Drawing Sheets

(51) Int. Cl.
*A61M 25/00* (2006.01)
*A61M 27/00* (2006.01)

(52) U.S. Cl.
CPC .............. *A61B 2017/3419* (2013.01); *A61B 2017/3456* (2013.01); *A61M 25/003* (2013.01); *A61M 27/00* (2013.01)

(58) Field of Classification Search
CPC .. A61B 2217/005; A61B 2017/320044; A61B 2017/06085; A61M 25/0194; A61M 2025/0197
See application file for complete search history.

(56) References Cited

U.S. PATENT DOCUMENTS

| | | | |
|---|---|---|---|
| 4,398,910 A | 8/1983 | Blake et al. | |
| 4,429,693 A | 2/1984 | Blake et al. | |
| 4,490,136 A | 12/1984 | Ekbladh et al. | |
| 4,565,545 A * | 1/1986 | Suzuki ................ | A61M 25/065 604/272 |
| 4,976,684 A | 12/1990 | Broadnax | |
| 5,123,910 A * | 6/1992 | McIntosh ......... | A61B 17/06066 606/223 |
| 5,562,696 A | 10/1996 | Nobles et al. | |
| 5,683,416 A * | 11/1997 | McGregor ....... | A61B 17/06066 223/102 |
| 5,944,732 A | 8/1999 | Raulerson et al. | |
| 5,968,022 A * | 10/1999 | Saito .................. | A61M 5/3286 604/272 |
| 8,105,313 B2 | 1/2012 | Schweikert et al. | |
| 9,248,257 B2 | 2/2016 | Martin et al. | |
| 9,289,232 B2 | 3/2016 | Massengale et al. | |
| 10,760,716 B1 * | 9/2020 | Currey ................... | B29C 65/66 |
| 2003/0176762 A1 * | 9/2003 | Kammerer ......... | A61B 17/0469 600/30 |
| 2004/0002724 A1 | 1/2004 | Falahee | |
| 2005/0234390 A1 | 10/2005 | Buckman et al. | |
| 2006/0173479 A1 * | 8/2006 | Smith ................ | A61B 1/00135 606/185 |
| 2006/0200183 A1 * | 9/2006 | Gardocki ................ | A61M 1/84 606/190 |
| 2007/0078396 A1 * | 4/2007 | Feeley .............. | A61M 39/0247 604/164.01 |
| 2007/0197981 A1 * | 8/2007 | Abe .................... | A61B 17/3415 604/272 |
| 2008/0234640 A1 * | 9/2008 | Fourie ................... | A61M 27/00 604/272 |
| 2008/0312677 A1 * | 12/2008 | Massengale ....... | A61B 17/3415 606/190 |
| 2009/0030438 A1 * | 1/2009 | Stulen ............ | A61B 17/320068 606/169 |
| 2009/0192512 A1 * | 7/2009 | Sommers ............... | A61B 17/68 606/64 |
| 2009/0216203 A1 * | 8/2009 | Ahn ..................... | A61M 5/3286 604/274 |
| 2009/0248071 A1 * | 10/2009 | Saint .................. | A61B 17/0401 606/232 |
| 2014/0194685 A1 * | 7/2014 | Riek .................. | A61B 17/3474 600/109 |
| 2014/0277073 A1 * | 9/2014 | Calderon .............. | A61M 29/00 606/198 |
| 2014/0364889 A1 * | 12/2014 | Stubber ............... | A61B 17/3415 606/185 |
| 2015/0257787 A1 * | 9/2015 | Haigh ................. | A61B 17/3468 600/309 |
| 2015/0320975 A1 | 11/2015 | Simpson et al. | |
| 2017/0298545 A1 * | 10/2017 | Tabibian .................. | D04B 3/02 |
| 2018/0085144 A1 * | 3/2018 | McGillicuddy .... | A61B 17/3423 |
| 2019/0085993 A1 * | 3/2019 | Nelson .................. | F16K 19/006 |

FOREIGN PATENT DOCUMENTS

| | | | |
|---|---|---|---|
| FR | 2161950 | 7/1973 | |
| GB | 2041999 A * | 9/1980 | ....... A61B 17/06066 |
| WO | 2009015016 | 1/2009 | |
| WO | 2015145768 | 10/2015 | |
| WO | 2015187477 | 12/2015 | |

\* cited by examiner

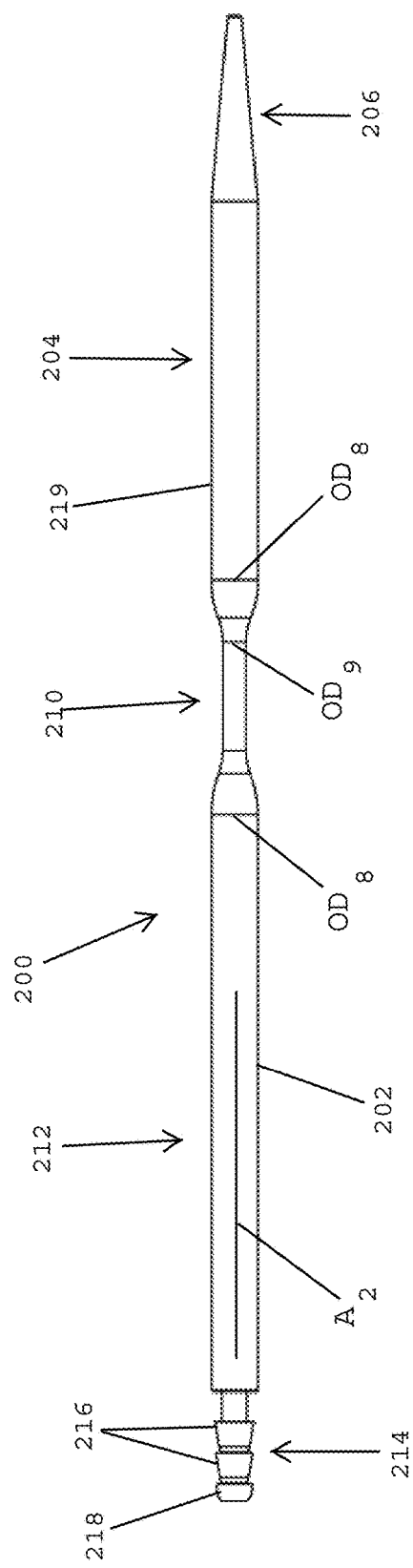
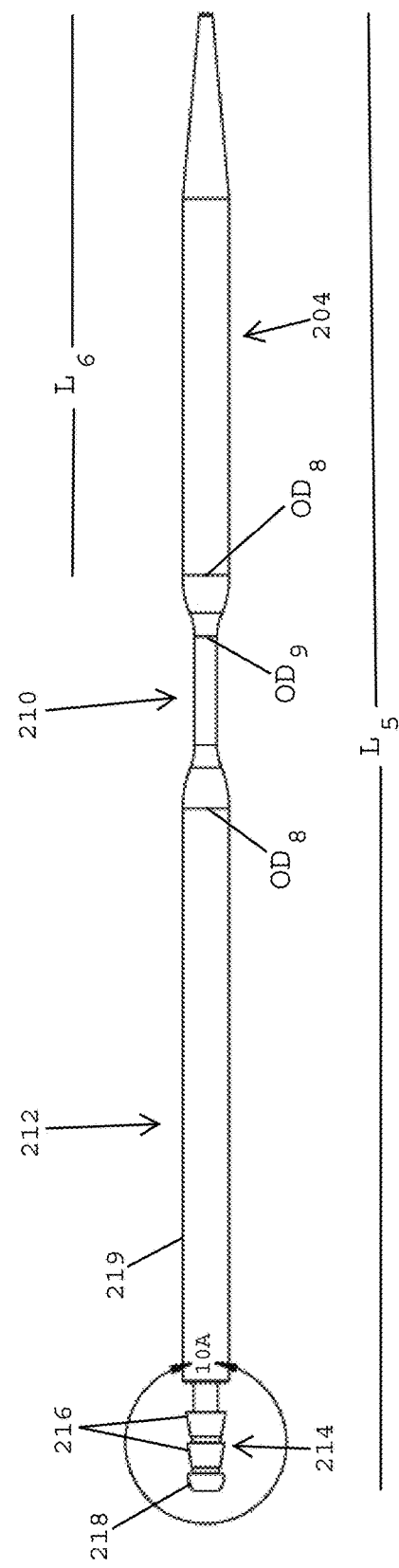
FIG. 7A
FIG. 7B

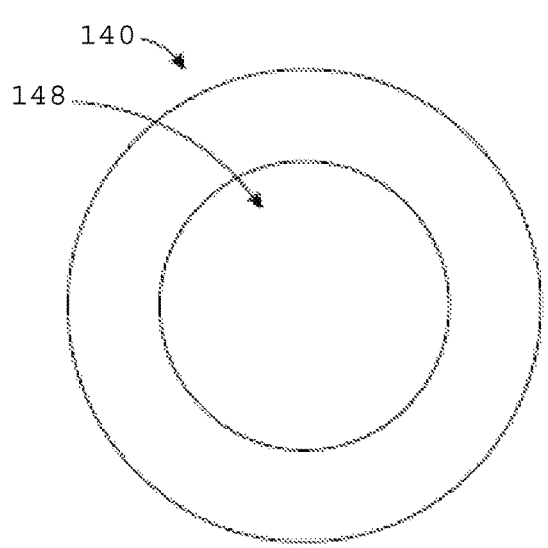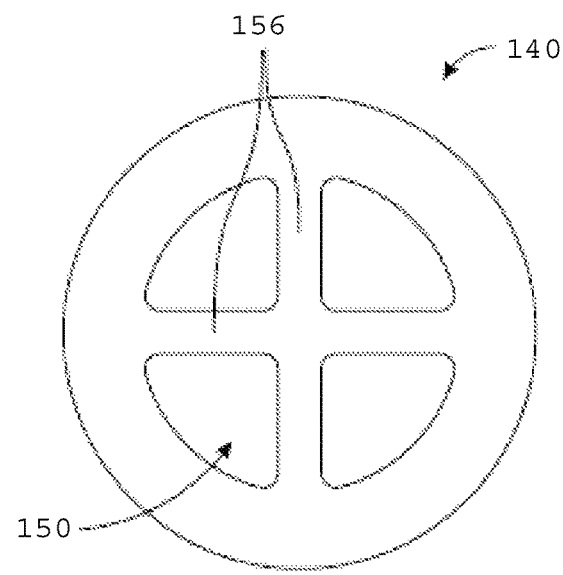
FIG. 23         FIG. 24
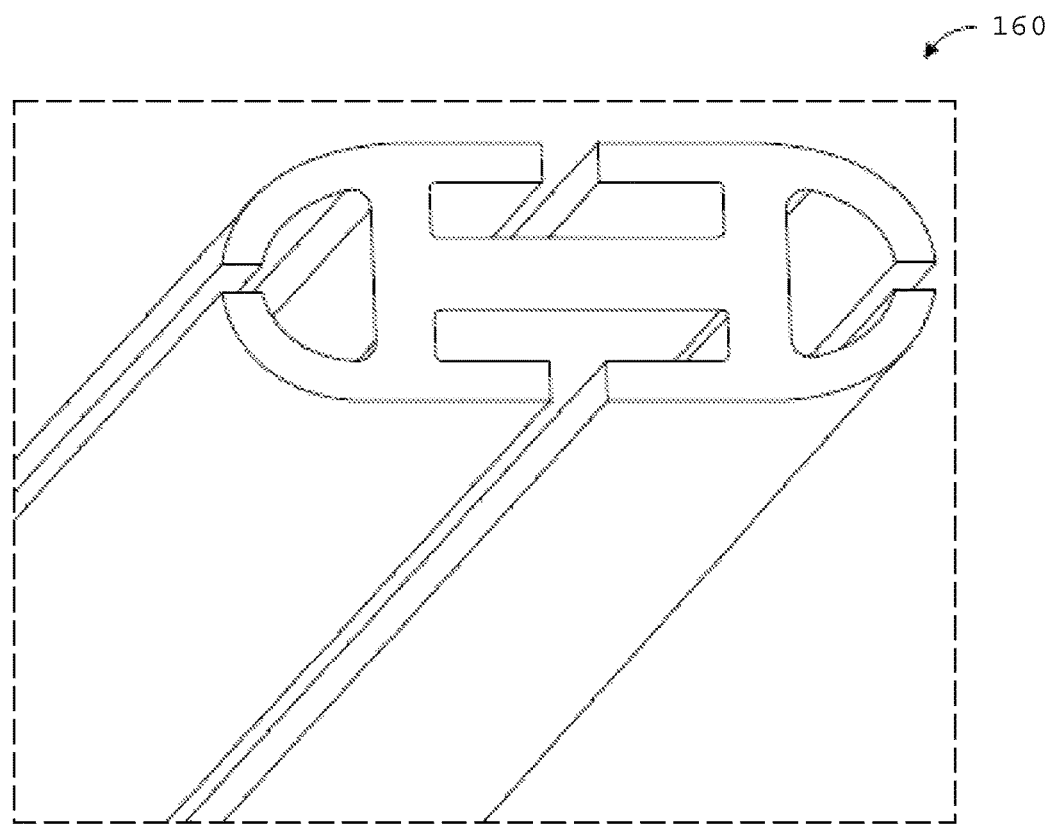
FIG. 25

BENDABLE TROCARS HAVING BLUNT TIPS AND CONNECTORS FOR ADVANCING WOUND DRAIN CATHETERS THROUGH TISSUE

BACKGROUND OF THE INVENTION

Field of the Invention

The present patent application is generally related to treating wounds, and is more specifically related to trocars used to advance wound drain catheters through tissue for safely and efficaciously draining fluids from wounds.

Description of the Related Art

Trocars are often used to insert wound drain catheters into a drainage site adjacent a surgical wound. Typically, a trocar has a wound drain catheter attached to an end of the trocar so that the tubing of the wound drain catheter follows the trocar along a path through the patient's body.

Several techniques may be used to insert a wound drain catheter in a patient's body. For example, a surgeon may simply place a drain and a small section of the wound drain catheter in the wound, close the incision, and suture around the wound drain catheter. This technique is somewhat unsatisfactory, since it is difficult to completely seal the area around the wound drain catheter by suturing, and thus, the wound may become infected. A more satisfactory technique is to pass a trocar, pre-attached to an end of the wound drain catheter, through healthy tissue by entering the patient's body at a point within the wound and exiting the body at an opening formed in skin. The surgeon uses the trocar to pull the wound drain catheter through the tissue until the wound drain catheter is properly positioned, with the drain located in the wound. Since the wound drain catheter exits the body at a point adjacent the wound, the wound can be completely closed by suturing, thereby reducing the risk of infection.

In some instances, when positioning a wound drain catheter at a wound site, the trocar and the wound drain catheter separate, leaving the end of the wound drain catheter in the patient's body. If this occurs, the wound drain catheter must be removed and the procedure repeated. Such separation is typically due to the difficulty of attaching the trocar to the wound drain catheter.

In some instances, trocars are manufactured with a slight bend near the sharpened tip of the trocar to allow the trocar to be manipulated through the tissue and/or skin of the patient. The wound drain catheter will follow the path made by the trocar until the drainage end of the wound drain catheter is located at a desired position within the body and the extension portion of the wound drain catheter is located outside the patient's body. At that stage, the trocar is separated from the wound drain catheter, whereupon the free end of the wound drain catheter is connected to a source of vacuum.

U.S. Pat. No. 4,398,910 discloses the use of a trocar in the manner described above. U.S. Pat. No. 4,359,053 discloses the fastening of plastic tubing to a trocar for the same purpose.

Trocars are typically made of very hard surgical grade stainless steel or other materials so that they may be sharpened to a very fine point to allow the sharpened tip of the trocar to pass through body tissue and skin. In many instances, it is difficult to properly position the wound drainage tubing because it is difficult to pass the trocar through the patient's body without hitting a solid structure such as bone. It is also desirable to avoid organs and sensitive tissue as the trocar advances through a patient.

U.S. Pat. No. 3,398,910 discloses a trocar that is manufactured to have a slight bend of about 15 degrees to allow the trocar to be manipulated through the body of the patient to correctly position the wound drain catheter at a location desired by the surgeon.

U.S. Pat. No. 4,976,684 to Broadnax, Jr. discloses a trocar that is used to insert wound drainage tubing into the body of a patient. The trocar has a sharpened tip and a shaft that is capable of being bent by a surgeon to a configuration that is desired by the surgeon, which allows easier and more accurate insertion of the wound drain catheter in the desired location in the patient's body. The trocar has an area of reduced cross section, located near the sharpened tip, which allows the trocar to be bent with a force that is generated by the hands of the surgeon.

The use of a trocar having a sharpened tip to introduce wound drain catheters in patients requires great care to assure that the sharpened tip of the trocar does not injure sensitive tissues of the patient (e.g., vessels and nerves).

Thus, there remains a need for trocars that may be used to introduce wound drain catheters in patients in a way that reduces the risk of unwanted tissue damage. There also remains a need for trocars that are readily bendable for passing through patients without injuring sensitive tissue and organs. In addition, there remains a need for trocars having blunt tips that minimize the possibility of tissue damage. Moreover, there remains a need for trocars that have a reduced diameter midsection that is located about midway between the leading end and the trailing end of the elongated shaft of the trocar. Further still, there remains a need for trocars that maintain reliable connections with wound drain catheters so that the trocars and wound drain catheters remain secured together during deployment.

SUMMARY OF THE INVENTION

In one embodiment, a trocar preferably includes an elongated shaft having a leading section, a trailing section, a reduced diameter midsection located between the leading and trailing sections, and a longitudinal axis extending from a leading end of the leading section to a trailing end of the trailing section of the elongated shaft. The trocars may have French sizes of about Fr 10-Fr 24.

In one embodiment, the leading section of the elongated shaft has a tapered region that terminates at a blunt tip located at the leading end of the elongated shaft. In one embodiment, a trocar having a blunt tip may help reduce a risk of unwanted puncturing of tissue and may also improve safety during use by a doctor, nurse, or other user.

In one embodiment, the trailing section of the elongated shaft has a connector located at the trailing end of the elongated shaft.

In one embodiment, the leading and trailing sections of the elongated shaft have a first diameter and the reduced diameter midsection of the elongated shaft has a second diameter that is smaller than the first diameter for enabling the elongated shaft to be bent at the reduced diameter midsection.

In one embodiment, the elongated shaft is made of various materials including but not limited to metals, biocompatible metals, medical grade steel, stainless steel, 303 stainless steel, and polymers.

In one embodiment, the leading and trailing sections of the elongated shaft are relatively more rigid than the reduced diameter midsection of the elongated shaft. In one embodiment, the reduced diameter midsection is more flexible, bendable and/or malleable than the leading and trailing sections of the elongated shaft.

In one embodiment, the elongated shaft includes an outer surface having a cylindrical shape. The elongated shaft may have cross-section having a circular shape.

In one embodiment, the tapered region includes a sloping surface that tapers away from the longitudinal axis of the elongated shaft.

In one embodiment, the blunt tip includes a flat surface having an outer perimeter. In one embodiment, the blunt tip has a convexly curved surface surrounding the outer perimeter of the flat surface and extending from the outer perimeter of the flat surface to the sloping surface of the tapered region.

In one embodiment, the sloping surface of the tapered region and the longitudinal axis of the elongated shaft cooperatively define an angle of about 3-5 degrees. In one embodiment, the flat surface of the blunt tip has an outer diameter of about 0.030-0.045 inches.

In one embodiment, the first diameter of the leading and trailing sections of the elongated shaft is about 0.125-0.250 inches, and the second diameter of the reduced diameter midsection is about 0.0875-0.0975 inches.

In one embodiment, the elongated shaft has a length of about 6 inches. In one embodiment, the leading section of the elongated shaft has a length of about 2.75 inches. In one embodiment, the tapered region of the leading section has a length of about 0.741 inches. In one embodiment, the reduced diameter midsection has a length of about 0.400-0.500 inches.

In one embodiment, the reduced diameter midsection is located midway between the leading and trailing ends of the elongated shaft.

In one embodiment, the connector includes an end knob having a curved surface, and one or more annular ridges located between the end knob and an end face at the trailing end of the trailing section of the elongated shaft.

In one embodiment, the end knob has an end knob outer diameter and the annular ridges have respective annular ridge outer diameters that are larger than the end knob outer diameter.

In one embodiment, a wound drain catheter may be secured to a trailing end of the trocar. In one embodiment, the wound drain catheter is a flexible tube made of a biocompatible material such as silicone. In one embodiment, the wound drain catheter has a first end and a second end. In one embodiment, the first end of the wound drain catheter is secured to the connector. In one embodiment, the wound drain catheter has an outer diameter that matches the first diameter of the leading and trailing sections of the elongated shaft. In one embodiment, a drain is secured to the second end of the flexible wound drain catheter.

In one embodiment, a trocar system preferably includes a shaft having a leading section, a trailing section, a reduced diameter midsection located between the leading and trailing sections, and a longitudinal axis extending from a leading end of the leading section to a trailing end of the trailing section of the elongated shaft. In one embodiment, the leading section of the shaft has a tapered region that terminates at a blunt tip located at the leading end thereof, and the trailing section of the shaft has a connector located at the trailing end thereof.

In one embodiment, the leading and trailing sections of the shaft have a first diameter and the reduced diameter midsection of the shaft has a second diameter that is smaller than the first diameter for enabling the shaft to be bent at the reduced diameter midsection.

In one embodiment, a first end of a flexible wound drain catheter is secured to the connector at the trailing end of the trailing section of the shaft. In one embodiment, the flexible wound drain catheter has an outer diameter that matches the first diameter of the leading and trailing sections of the shaft.

In one embodiment, the tapered region of the leading section of the elongated shaft preferably includes a sloping surface that tapers away from the longitudinal axis of the elongated shaft.

In one embodiment, the blunt tip desirably includes a flat surface. In one embodiment, the flat surface is orthogonal to the longitudinal axis of the elongated shaft of the trocar. In one embodiment, the flat surface of the blunt tip has an outer perimeter and a convexly curved surface surrounding the outer perimeter of the flat surface and extending from the outer perimeter of the flat surface to the sloping surface of the tapered region.

In one embodiment, a method for draining fluid from a mammal preferably includes attaching a flexible wound drainage catheter to a trocar. In one embodiment, the trocar may have an elongated shaft including a leading section, a trailing section, a reduced diameter midsection located between the leading and trailing sections, and a longitudinal axis extending from a leading end of the leading section to a trailing end of the trailing section of the elongated shaft.

In one embodiment, the leading section of the elongated shaft preferably has a tapered region that terminates at a blunt tip located at the leading end thereof. In one embodiment, the trailing section of the elongated shaft preferably has a connector located at the trailing end thereof.

In one embodiment, the leading and trailing sections of the elongated shaft desirably have a first diameter and the reduced diameter midsection of the elongated shaft has a second diameter that is smaller than the first diameter for enabling the elongated shaft to be bent at the reduced diameter midsection In one embodiment, the method preferably includes bending the trocar to an angulated configuration, and after the bending the trocar, passing the trocar through skin of a mammal, whereby the trocar maintains the angulated configuration while passing through the skin of the mammal.

In one embodiment, the method preferably includes passing the trocar out of the skin of the mammal, while maintaining the flexible wound drain catheter within the mammal.

In one embodiment, the method includes draining fluid from the mammal through the flexible wound drain catheter, such as by coupling a source of vacuum to an end of the wound drain catheter that extends outside the body of the patient.

In one embodiment, a method of implanting wound drain catheter may include bluntly dissecting tissue starting from the inside of a body cavity to create a partial pathway toward the skin layer, introducing the blunt point of a trocar carrying a wound drain catheter into the partial pathway, using a sharp instrument to create a small incision in the skin at the location where the blunt point of the trocar will emerge, advancing the trocar through the incision, and detaching the wound drain catheter from the trocar.

In one embodiment, the tapered region of the leading section of the elongated shaft includes a sloping surface that tapers away from the longitudinal axis of the elongated shaft. In one embodiment, the blunt tip preferably includes a flat surface having an outer perimeter and a convexly curved surface surrounding the outer perimeter of the flat surface and extending from the outer perimeter of the flat surface to the sloping surface of the tapered region.

In one embodiment, the first diameter of the leading and trailing sections of the elongated shaft is about 0.125-0.250 inches, and the second diameter of the reduced diameter midsection is about 0.0875-0.0975 inches.

In one embodiment, the elongated shaft of the trocar preferably has a length of about 6 inches, the leading section of the elongated shaft has a length of about 2.75 inches, the tapered region of the leading section has a length of about 0.741 inches, and the reduced diameter midsection has a length of about 0.400-0.500 inches.

These and other preferred embodiments of the present patent application will be described in more detail herein.

BRIEF DESCRIPTION OF THE DRAWINGS

FIG. 7A is a side view of the trocar shown in FIG. 6.

FIG. 7B is another side view of the trocar shown in FIG. 6.

FIG. 23 is a cross-sectional view of the flute section of the wound drain catheter shown in FIG. 22.

FIG. 24 is a cross-sectional view of the transition section of the wound drain catheter shown in FIG. 22.

FIG. 25 shows a perspective view of an end of a drain that is securable to a wound drain catheter, in accordance with one embodiment of the present patent application.

DETAILED DESCRIPTION OF PREFERRED EMBODIMENTS

Figure 1:
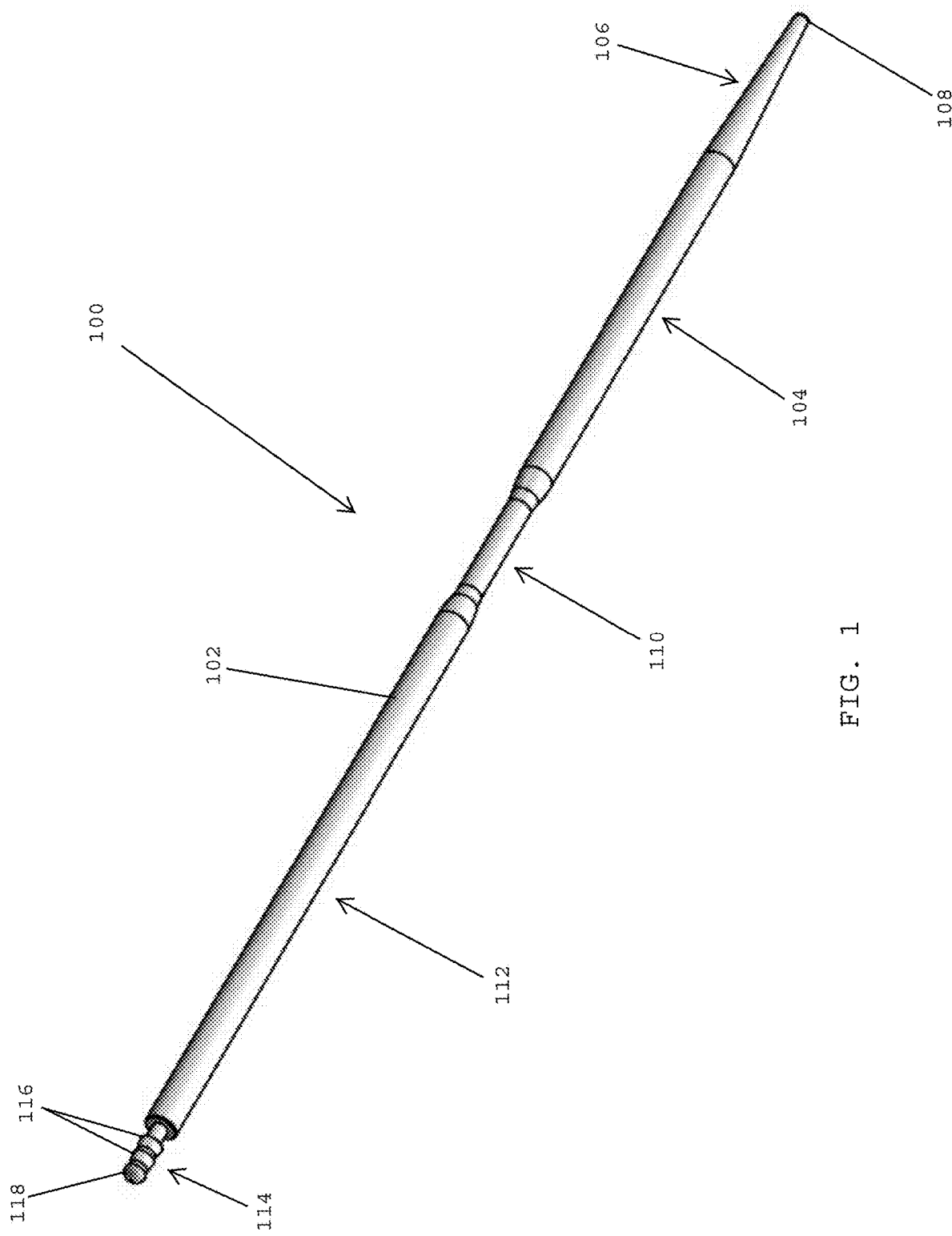
FIG. 1 is a perspective view of a trocar having a leading section including a tapered region that terminates at a blunt tip, a reduced diameter midsection, and a trailing section including a connector, in accordance with one embodiment of the present patent application.

Referring to FIG. 1, in one embodiment, a trocar 100 for conveying a wound drain catheter through tissue preferably includes an elongated shaft 102 having a leading section 104 with a tapered region 106 including a blunt tip 108 at a free end thereof, a reduced diameter midsection 110, and a trailing section 112 having a connector 114 including annular ridges 116 and an end knob 118. In one embodiment, the blunt tip 108 is desirably at the most leading end of the elongated shaft and the connector 114 is at the most trailing end of the elongated shaft. In one embodiment, providing the blunt tip 108 at the leading end of the trocar may help reduce the risk of unwanted puncturing of tissue and may also improve safety during use by a doctor, nurse, or other user. In one embodiment, the trocar 100 may be made of metal or polymer materials. In one embodiment, the trocar 100 is made of a biocompatible metal, such as stainless steel. In one embodiment, the trocar 100 may be made of a stainless steel material commonly referred to as 303 stainless steel.

Figure 2A:
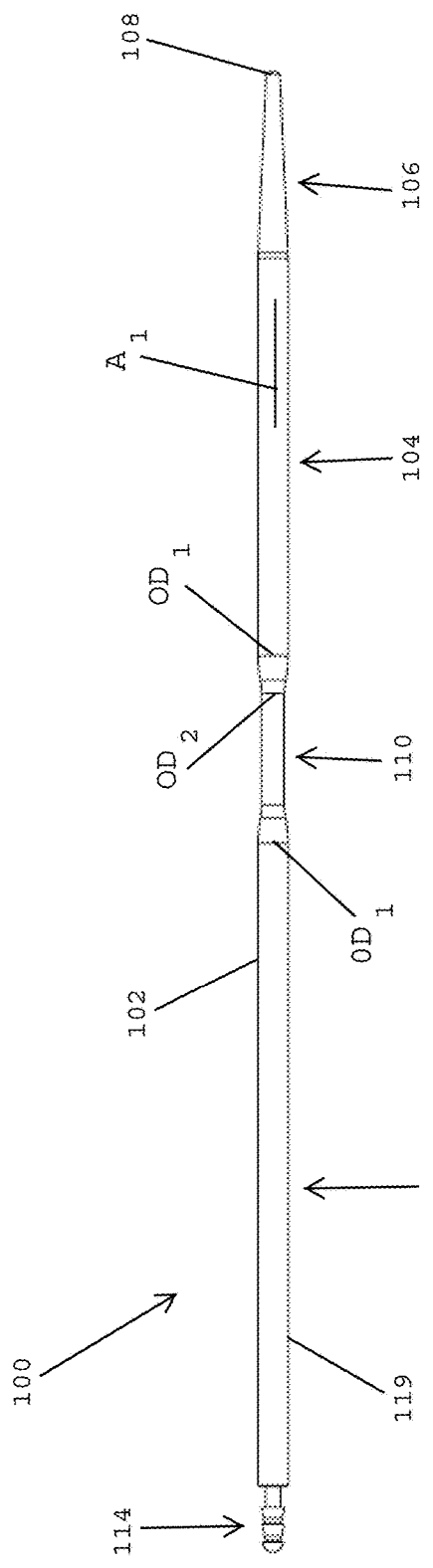
FIG. 2A is a side view of the trocar shown in FIG. 1.
Figure 2B:
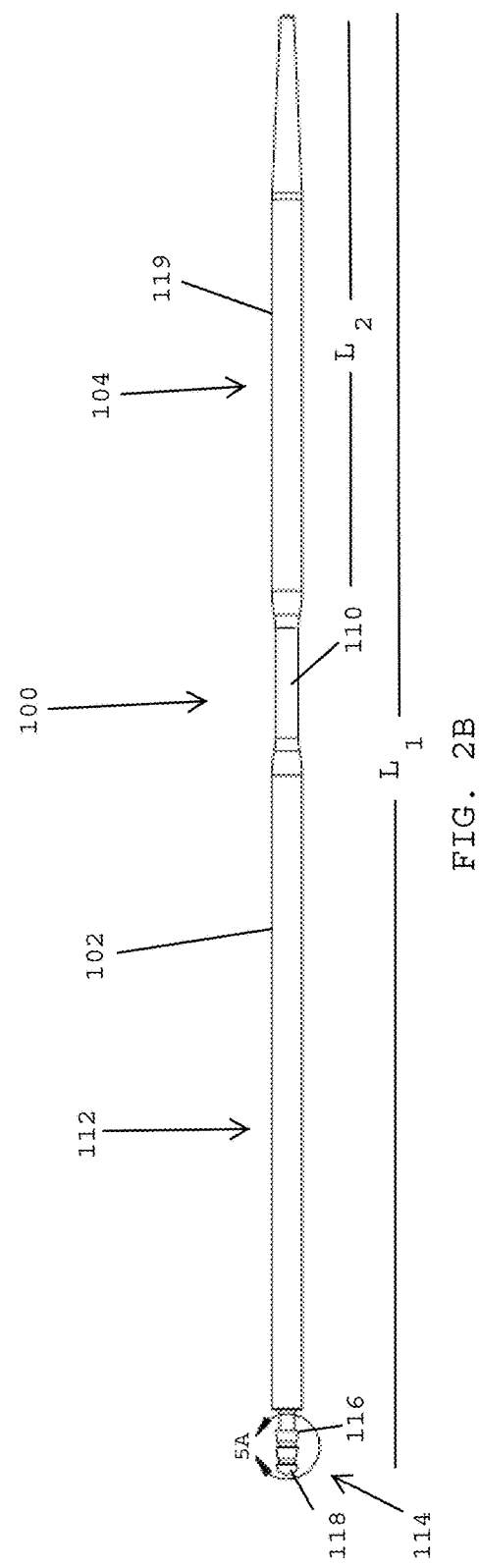
FIG. 2B is another side view of the trocar shown in FIG. 1.

Referring to FIGS. 2A and 2B, in one embodiment, the elongated shaft 102 of the trocar 100 desirably has a longitudinal axis $A_1$ that extends along the length of the elongated shaft 102 from the connector 114 at the trailing section 112 of the shaft to the blunt tip 108 at the leading section 104 of the shaft 102. In one embodiment, the elongated shaft 102 of the trocar preferably has a length $L_1$ of about 4-8 inches and more preferably about 6 inches. In one embodiment, the leading section 104 of the elongated shaft 102 has a length $L_2$ of about 1-4 inches and more preferably about 2.50 inches.

In one embodiment, the French size (Fr) of the trocar 100 is between Fr 10 and Fr 24. In one embodiment, the elongated shaft 102 desirably includes an outer surface 119 having a cylindrical shape. In one embodiment, the leading and trailing sections 104, 112 of the elongated shaft 102 define a first outer diameter $OD_1$ that is greater than a second outer diameter $OD_2$ of the reduced diameter midsection 110. In one embodiment, the larger first outer diameter $OD_1$ is about 0.125 inches (e.g., Fr 10) and the smaller second outer diameter $OD_2$ is about 0.092 inches. As will be described in more detail herein, the reduced diameter midsection 110 interconnects the trailing section 112 and the leading section 104 of the elongated shaft 102. Thus, the reduced diameter midsection 110 is more bendable than the leading and trailing sections of the shaft so that the leading section 104 of the shaft 102 may be bent at different angles relative to the trailing section 112 of the shaft 102. In one embodiment, all of the bending of the trocar desirably occurs within the reduced diameter midsection 110 region of the trocar. In one embodiment, as the leading section 104 is angulated relative to the trailing section 112, the leading and trailing sections preferably maintain a straight configuration.

Referring to FIG. 2B, in one embodiment, the connector 114 located at the trailing end of the trailing section 112 of the elongated shaft 102 desirably includes annular ridges 116 that are adapted to engage with an inner surface of a wound drain catheter for connecting the wound drain catheter to the trailing section 112 of the trocar 100. The connector 114 desirably includes an end knob 118 that is adapted for insertion into an opening or conduit accessible at an end of a wound drain catheter for connecting the trocar 100 with the drain catheter.

Figure 3A:
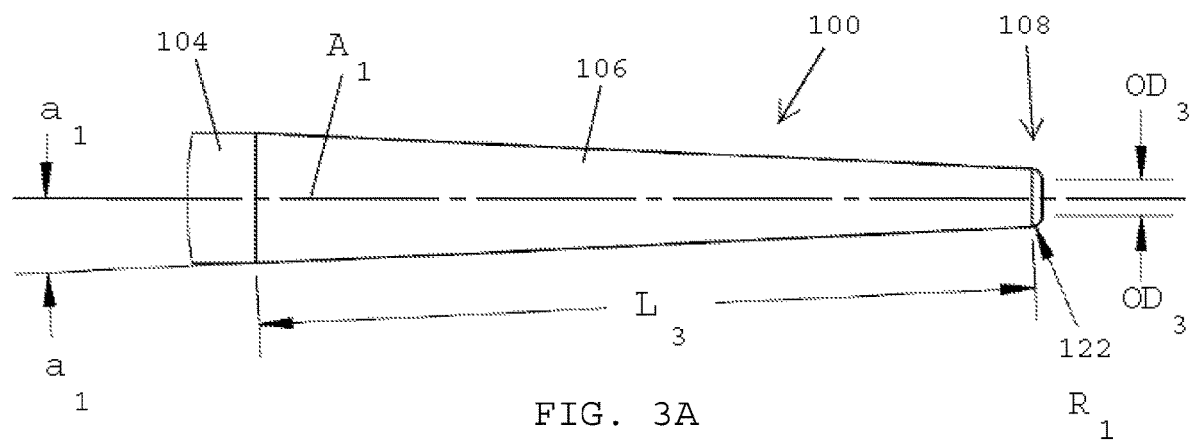
FIG. 3A is a side view of the tapered region and the blunt tip at the leading end of the trocar shown in FIG. 1.
Figure 3B:
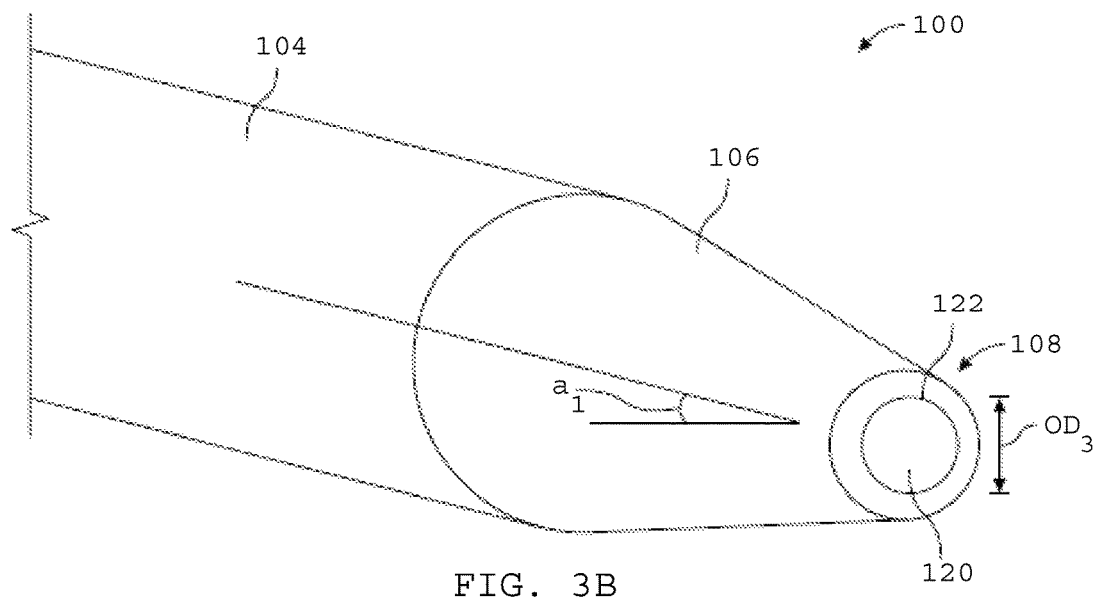
FIG. 3B is a perspective view of the tapered region and the blunt tip at the leading end of the trocar shown in FIG. 1.
Figure 3C:
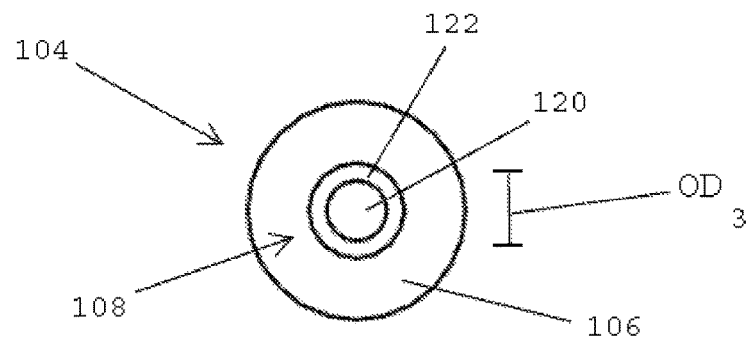
FIG. 3C is an end view of the tapered region and the blunt tip at the leading end of the trocar shown in FIG. 1.

Referring to FIGS. 3A-3C, in one embodiment, the leading section 104 (FIG. 1) of a trocar preferably includes the tapered region 106 that tapers inwardly to the blunt tip 108. In one embodiment, the blunt tip 108 preferably has a flat end surface 120 having an outer diameter $OD_3$ of about 0.035 inches. The blunt tip 108 preferably includes a curved surface 122, such as a convexly curved surface, that extends between the outer perimeter of the flat end surface 120 and the sloping sidewalls of the tapered region 106 of the leading section 104 of the trocar 100. In one embodiment, the curved surface 122 has a radius $R_1$ of about 0.010 inches.

In one embodiment, the tapered region 106 of the leading section 104 tapers outwardly from the blunt tip 108. In one embodiment, the tapered region 106 of the leading section 104 of the trocar has a length $L_3$ of about 0.741 inches. In one embodiment, the sloping outer surfaces of the tapered region 106 define an angle $\alpha_1$ of about three-five degrees and more preferably about three degrees (3°) relative to the longitudinal axis $A_1$ of the trocar 100.

Figure 4A:
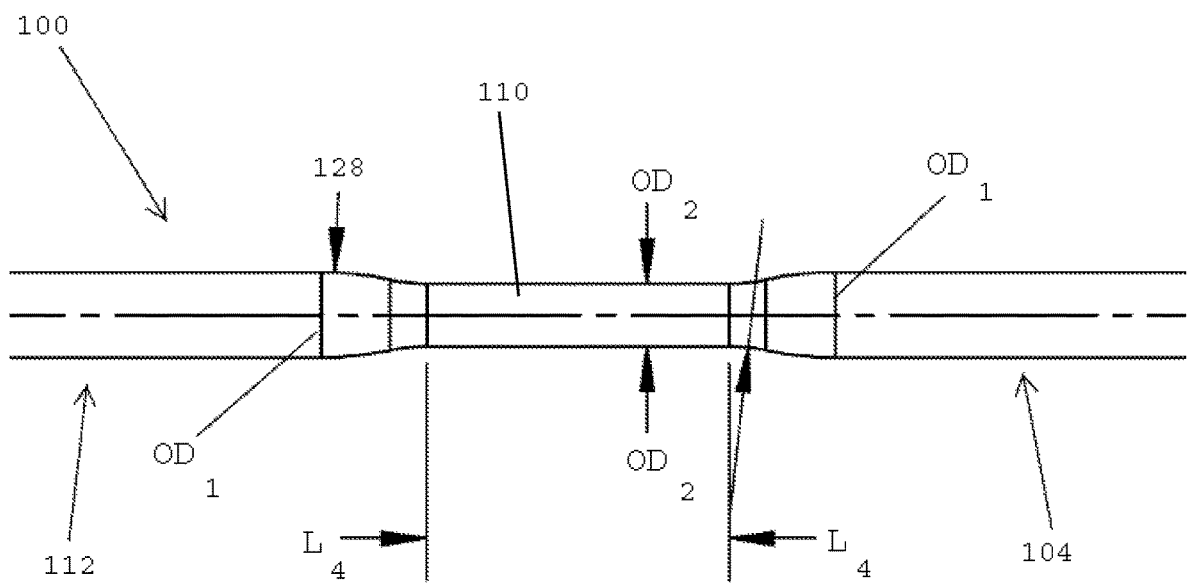
FIG. 4A is a side view of the reduced diameter midsection of the trocar shown in FIG. 1.
Figure 4B:
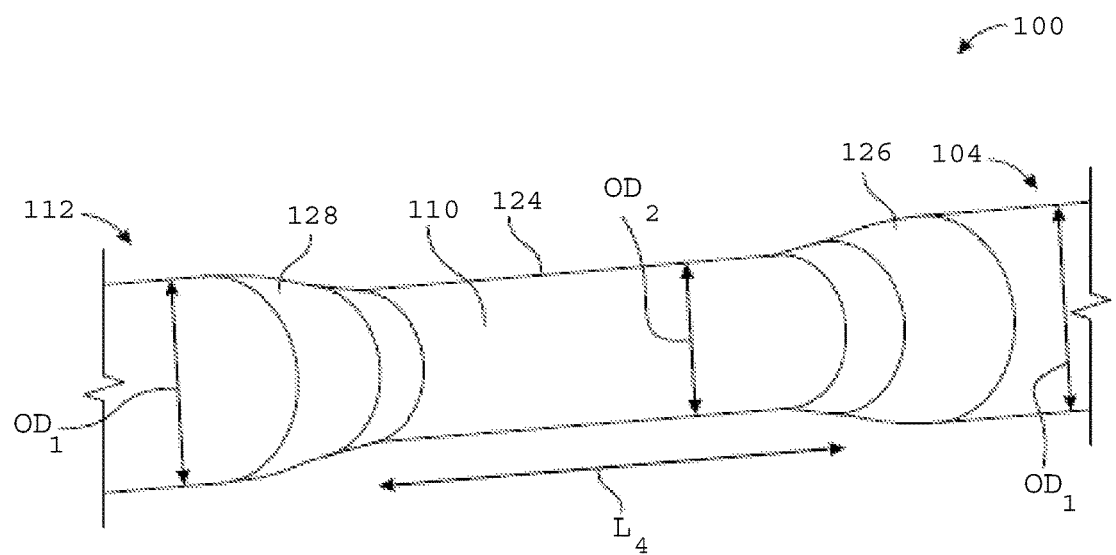
FIG. 4B is a perspective view of the reduced diameter midsection of the trocar shown in FIG. 1.

Referring to FIGS. 4A and 4B, in one embodiment, the reduced diameter midsection 110 of the trocar 100 desirably has an outer cylindrical surface 124 that defines the second outer diameter $OD_2$ of about 0.092 inches, which is less than the respective first outer diameters $OD_1$ of the leading section 104 and the trailing section 112 of the elongated shaft 102 of the trocar 100. A leading end of the reduced diameter midsection 110 preferably has a first shoulder 126 that slopes or tapers outwardly between the smaller, second outer diameter $OD_2$ of the reduced diameter midsection 124 and the larger, first outer diameter $OD_1$ of the leading section 104 of the elongated shaft of the trocar. In addition, a trailing end of the reduced diameter midsection 110 has a second shoulder 128 that slopes or tapers outwardly between the smaller, second outer diameter $OD_2$ of the reduced diameter midsection 110 and the larger, second outer diameter $OD_1$ of the trailing section 112 of the elongated shaft 102. In one embodiment, the reduced diameter midsection 110 of the trocar 100 has a length of $L_4$ of about 0.40-0.50 inches and more preferably about 0.440 inches.

Figure 5A:
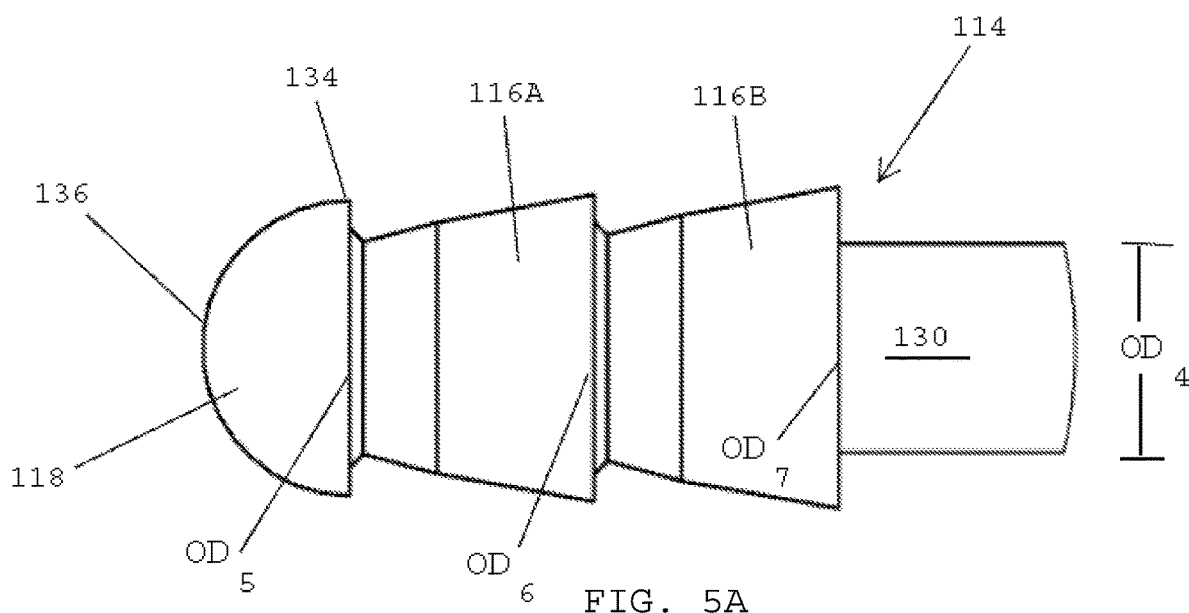
FIG. 5A is a side view of the connector at the trailing section of the trocar shown in FIG. 1.
Figure 5B:
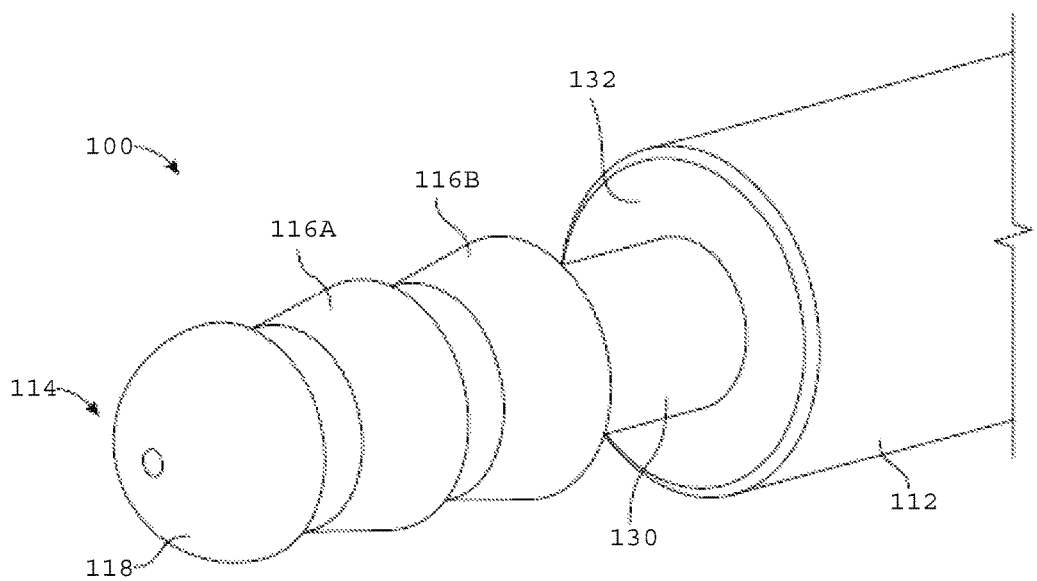
FIG. 5B is a perspective view of the connector at the trailing section of the trocar shown in FIG. 1.
Figure 5C:
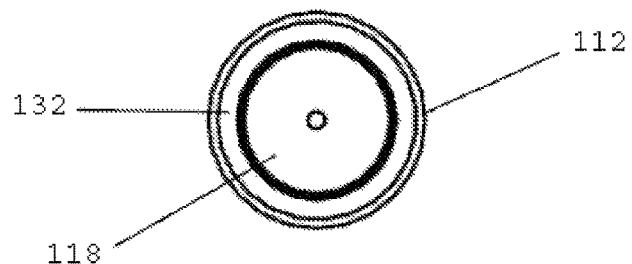
FIG. 5C is an end view of the connector at the trailing section of the trocar shown in FIG. 1.

Referring to FIGS. 5A-5C, in one embodiment, the connector 114 projecting from the trailing end of the trailing section 112 (FIG. 1) of the trocar 100 desirably includes annular ridges 116A, 116B that project outwardly from a stem 130 that is connected with an end face 132 at the trailing end of the trailing section 112 of the trocar 100. In one embodiment, the stem 130 has an outer diameter $OD_4$ of about 0.060 inches. In one embodiment, the end knob 118 has a base 134 defining the largest diameter section of the end knob. In one embodiment, the base 134 defines an outer diameter $OD_5$ of about 0.085 inches. In one embodiment, the first ridge 116A defines an outer diameter $OD_6$ of about 0.088 inches. In one embodiment, the second ridge 116 defines an outer diameter $OD_7$ of about 0.092 inches. Thus, in one embodiment, the respective outer diameters of the end knob 118 and the first and second annular ridges 116A, 116B increase slightly in series between the end knob 118 and the second annular ridge 116B. For example, the first annular ridge has a larger outer diameter than the end knob, and the second annular ridge has a larger outer diameter than the first annular ridge. In one embodiment, the end knob 118 preferably has a curved, hemispherical-shaped surface 136.

Figure 6:
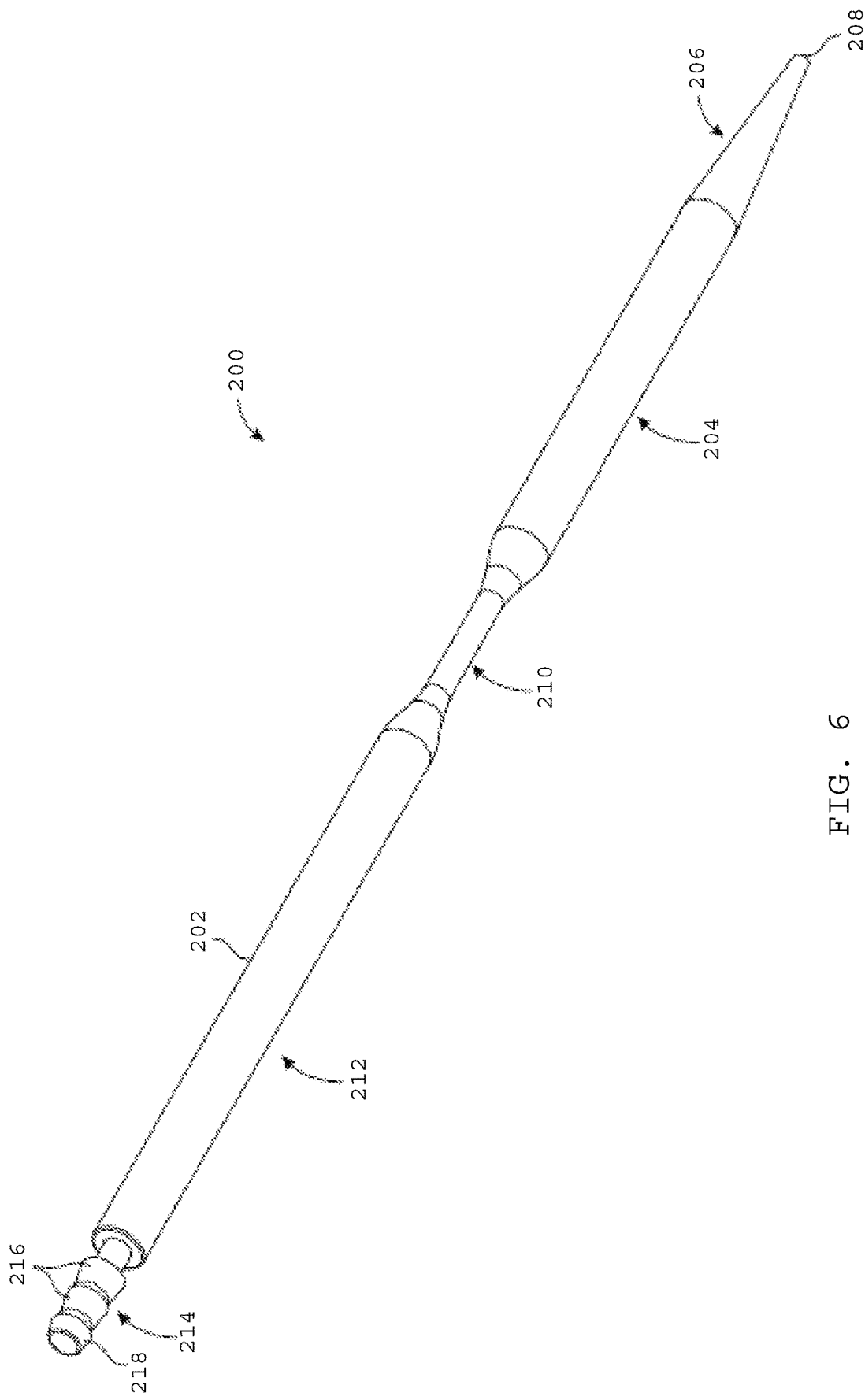
FIG. 6 is a perspective view of a trocar having a leading section including a tapered region that terminates at a blunt tip, a reduced diameter midsection, and a trailing section including a connector, in accordance with one embodiment of the present patent application.

Referring to FIG. 6, in one embodiment, a trocar 200 for conveying a wound drain catheter through tissue preferably includes an elongated shaft 202 having a leading section 204 with a tapered region 206 including a blunt tip 208 at a free end thereof, a reduced diameter midsection 210, and a trailing section 212 having a connector 214 including one or more annular ridges 216 and an end knob 218. In one embodiment, the trocar may be made of metal such as stainless steel, and more preferably 303 stainless steel.

Referring to FIGS. 7A and 7B, in one embodiment, the elongated shaft 202 of the trocar 200 desirably has a longitudinal axis $A_2$ that extends along the length of the elongated shaft 202 from the connector 214 at the trailing section 212 of the shaft to the blunt tip 208 at the leading end of the elongated shaft 202. In one embodiment, the elongated shaft 202 of the trocar has a length $L_5$ of about 5-7 inches and more preferably about 6 inches. In one embodiment, the leading section 204 of the elongated shaft 202 has a length $L_6$ of about 2-3 inches and more preferably about 2.50 inches.

In one embodiment, the trocar 200 may have a size of Fr 10-Fr 24 and more preferably about Fr 15. In one embodiment, the elongated shaft 202 desirably includes an outer surface 219 having a cylindrical shape. In one embodiment, the leading and trailing sections 204, 212 of the elongated shaft 202 define a first outer diameter $OD_8$ that is greater than a second outer diameter $OD_9$ of the reduced diameter midsection 210. In one embodiment, the larger first outer diameter $OD_8$ is about 0.188 inches and the smaller second outer diameter $OD_9$ is about 0.0925 inches. As will be described in more detail herein, the reduced diameter midsection 210 interconnects the trailing section 212 and the leading section 204 of the elongated shaft 202. The reduced diameter midsection 210 is more flexible and/or bendable than the leading and trailing sections of the shaft so that the leading section 204 of the shaft 202 may be bent at different angles relative to the trailing section 212 of the shaft 202. In one embodiment, all of the bending of the trocar desirably occurs within the reduced diameter midsection 210 region. In one embodiment, as the leading section 204 is angulated relative to the trailing section 212, the leading and trailing sections preferably maintain a straight configuration.

Referring to FIG. 7B, in one embodiment, the connector 214 located at the trailing section 212 of the elongated shaft 202 desirably includes one or more annular ridges 216 that are adapted to engage with an inner surface of a wound drain catheter for connecting the wound drain catheter to the trailing section 212 of the trocar 200. The connector 214 desirably includes an end knob 218 that is inserted into an opening or conduit accessible at an end of a wound drain catheter for connecting a wound drain catheter to the trailing section of the trocar. In one embodiment, the outer diameter of the wound drain catheter preferably matches the French size of the trocar.

Figure 8A:
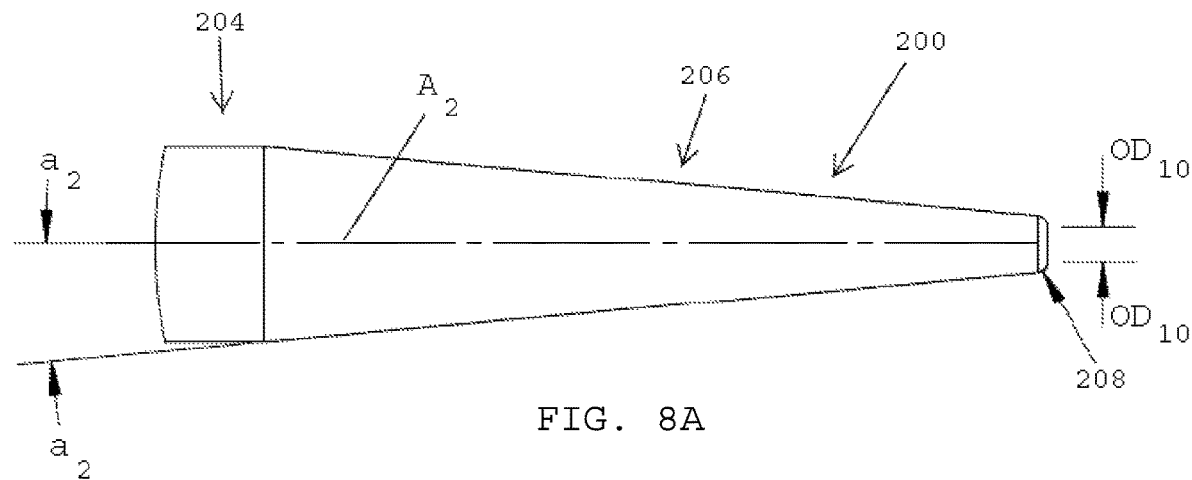
FIG. 8A is a side view of the tapered region and the blunt tip at the leading end of the trocar shown in FIG. 6.
Figure 8B:
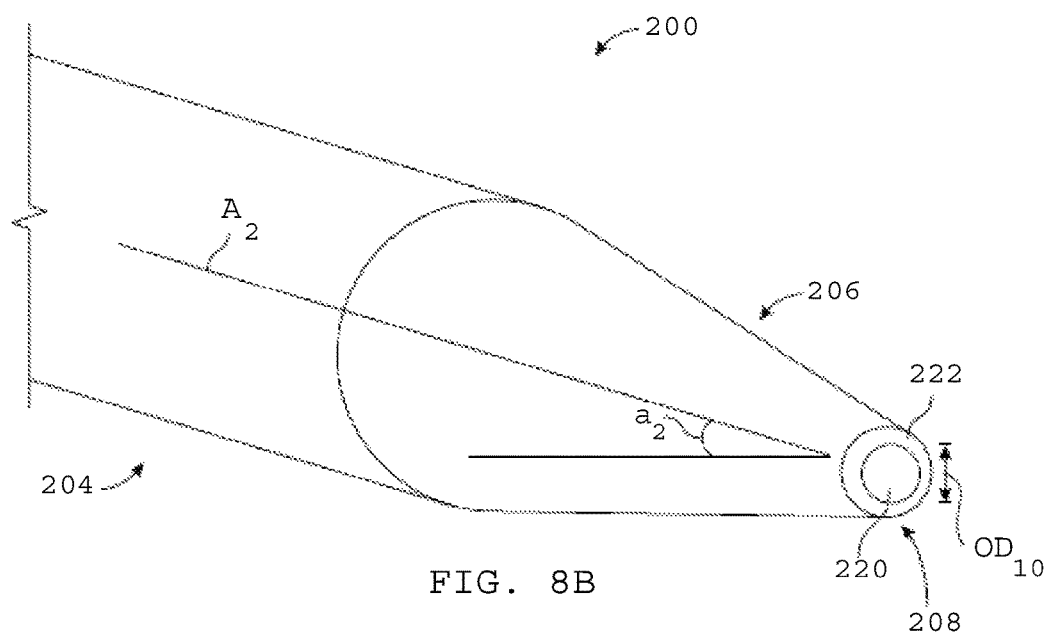
FIG. 8B is a perspective view of the tapered region and the blunt tip at the leading end of the trocar shown in FIG. 6.
Figure 8C:
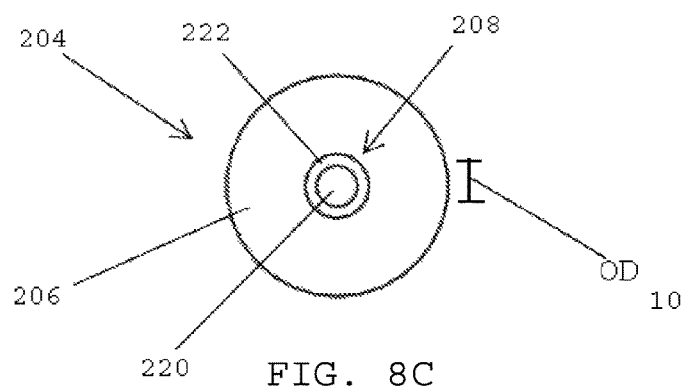
FIG. 8C is an end view of the tapered region and the blunt tip at the leading end of the trocar shown in FIG. 6.

Referring to FIGS. 8A-8C, in one embodiment, the leading section 204 (FIG. 1) of the elongated shaft of the trocar preferably includes the tapered region 206 that tapers inwardly to the blunt tip 208. In one embodiment, the blunt tip 208 preferably has a flat end surface 220 having an outer diameter $OD_{10}$ of about 0.035 inches. The blunt tip 208 preferably includes a curved surface 222, such as a convexly curved surface, that extends between the outer perimeter of the flat end surface 220 and the sloping sidewalls of the tapered region 206 of the leading section 204 of the trocar 200. In one embodiment, the curved surface 222 has a radius $R_2$ of about 0.010 inches.

In one embodiment, the tapered region 206 of the leading section 204 tapers outwardly from the blunt tip 208. In one embodiment, the tapered region 206 of the leading section 204 of the trocar has a length $L_7$ of about 0.741 inches. In one embodiment, the sloping outer surface of the tapered region 206 defines an angle $\alpha_2$ of about three-five degrees and more preferably about four degrees (4°) relative to the longitudinal axis $A_2$ of the elongated shaft of the trocar 200.

Figure 9A:
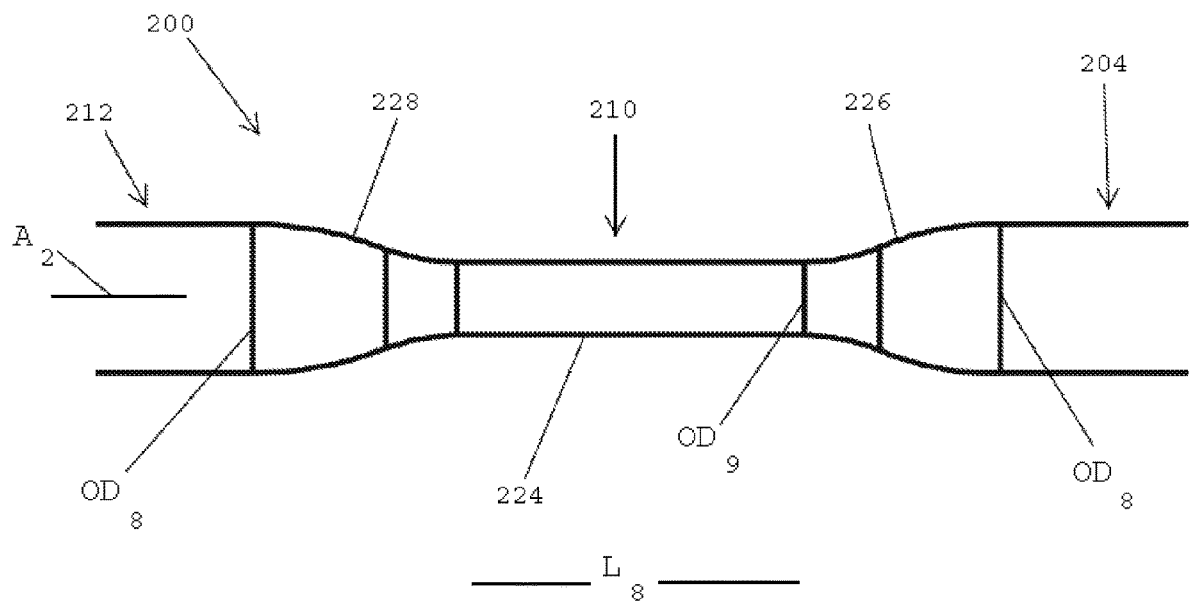
FIG. 9A is a side view of the reduced diameter midsection of the trocar shown in FIG. 6.
Figure 9B:
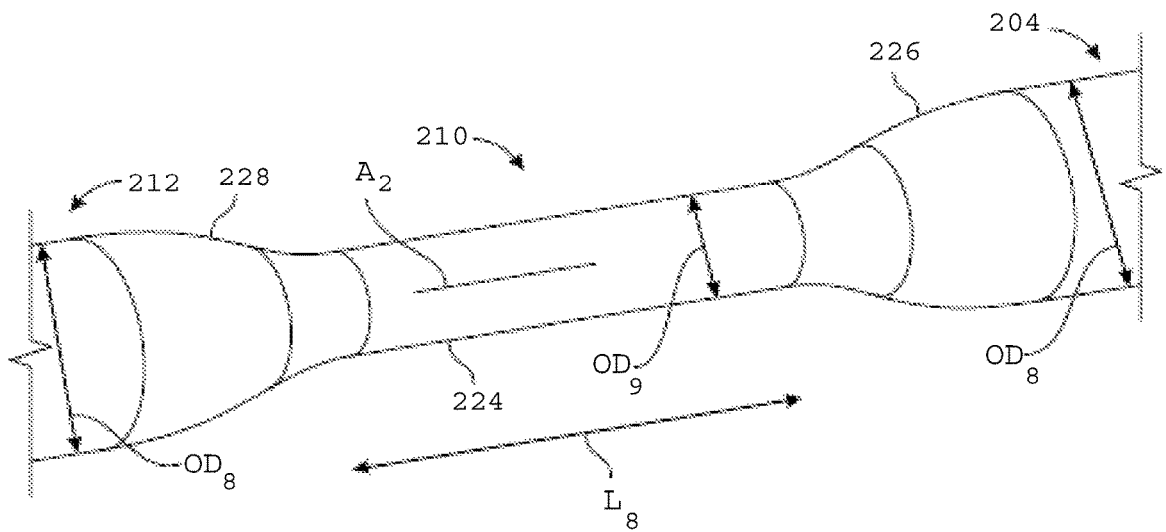
FIG. 9B is a perspective view of the reduced diameter midsection of the trocar shown in FIG. 6.

Referring to FIGS. 9A and 9B, in one embodiment, the reduced diameter midsection 210 of the trocar 200 desirably has an outer cylindrical surface 224 that defines the second outer diameter $OD_9$ of about 0.0925 inches, which is less than the respective first outer diameters $OD_8$ of about 0.188 inches of the leading and trailing sections 204, 212 of the elongated shaft of the trocar 200. The leading end of the reduced diameter midsection 210 preferably has a first shoulder 226 that slopes or tapers outwardly between the second outer diameter $OD_9$ of the reduced diameter midsection 210 and the larger, first outer diameter $OD_8$ of the leading section 204 of the elongated shaft of the trocar. In one embodiment, the trailing end of the reduced diameter midsection 210 has a second shoulder 228 that slopes or tapers outwardly between the smaller, second outer diameter $OD_9$ of the reduced diameter midsection 210 and the larger, second outer diameter $OD_8$ of the trailing section 212 of the elongated shaft 202. In one embodiment, the reduced diameter midsection 210 of the trocar 200 has a length of $L_8$ of about 0.40-0.50 inches and more preferably about 0.440 inches.

Figure 10A:
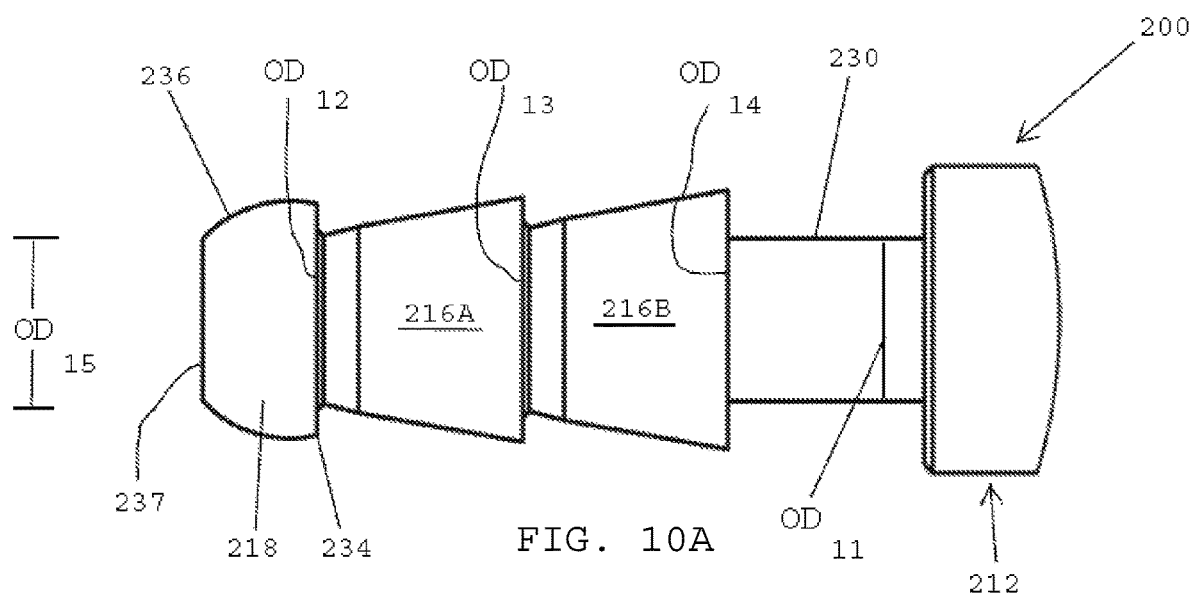
FIG. 10A is a side view of the connector at the trailing end of the trocar shown in FIG. 6.
Figure 10B:
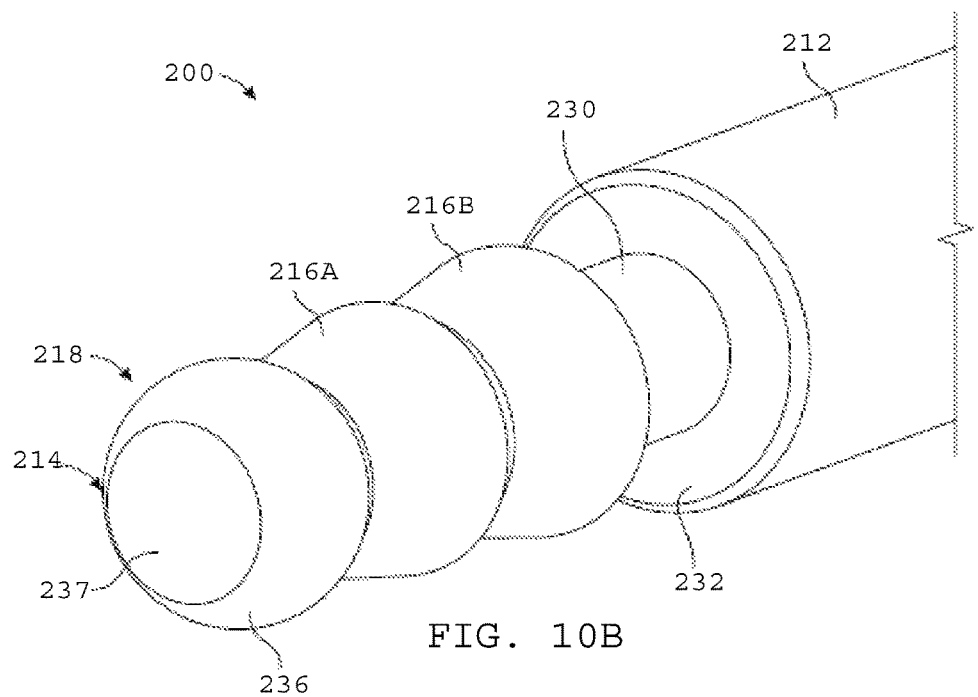
FIG. 10B is a perspective view of the connector at the trailing end of the trocar shown in FIG. 6.
Figure 10C:
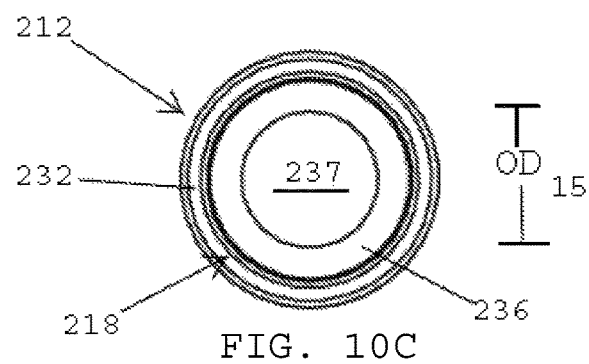
FIG. 10C is an end view of the connector at the trailing end of the trocar shown in FIG. 6.

Referring to FIGS. 10A-10C, in one embodiment, the connector 214 at the trailing section 212 (FIG. 6) of the trocar desirably includes annular ridges 216A, 216B that project outwardly from a stem 230 that is connected with an end face 232 at the trailing end of the trailing section 212 of the elongated shaft of the trocar 200. In one embodiment, the stem 230 has an outer diameter $OD_{11}$ (FIG. 10A) of about 0.100 inches. In one embodiment, the end knob 218 has a base 234 that defines the largest diameter section of the end knob. In one embodiment, the base 234 defines an outer diameter $OD_{12}$ (FIG. 10A) of about 0.142 inches. In one embodiment, the first ridge 216A defines an outer diameter $OD_{13}$ (FIG. 10A) of about 0.150 inches. In one embodiment, the second ridge 216B defines an outer diameter $OD_{14}$ (FIG. 10A) of about 0.159 inches. Thus, in one embodiment, the respective outer diameters of the end knob 218 and the first and second annular ridges 216A, 216B increase in series between the end knob 218 and the second annular ridge 216B. For example, the first annular ridge has a larger diameter than the end knob, and the second annular ridge has a larger diameter than the first annular ridge. In one embodiment, the end knob 218 preferably has a curved surface 236 and a flat end surface 237 having an outer diameter $OD_{15}$ of about 0.100 inches.

Figure 11:
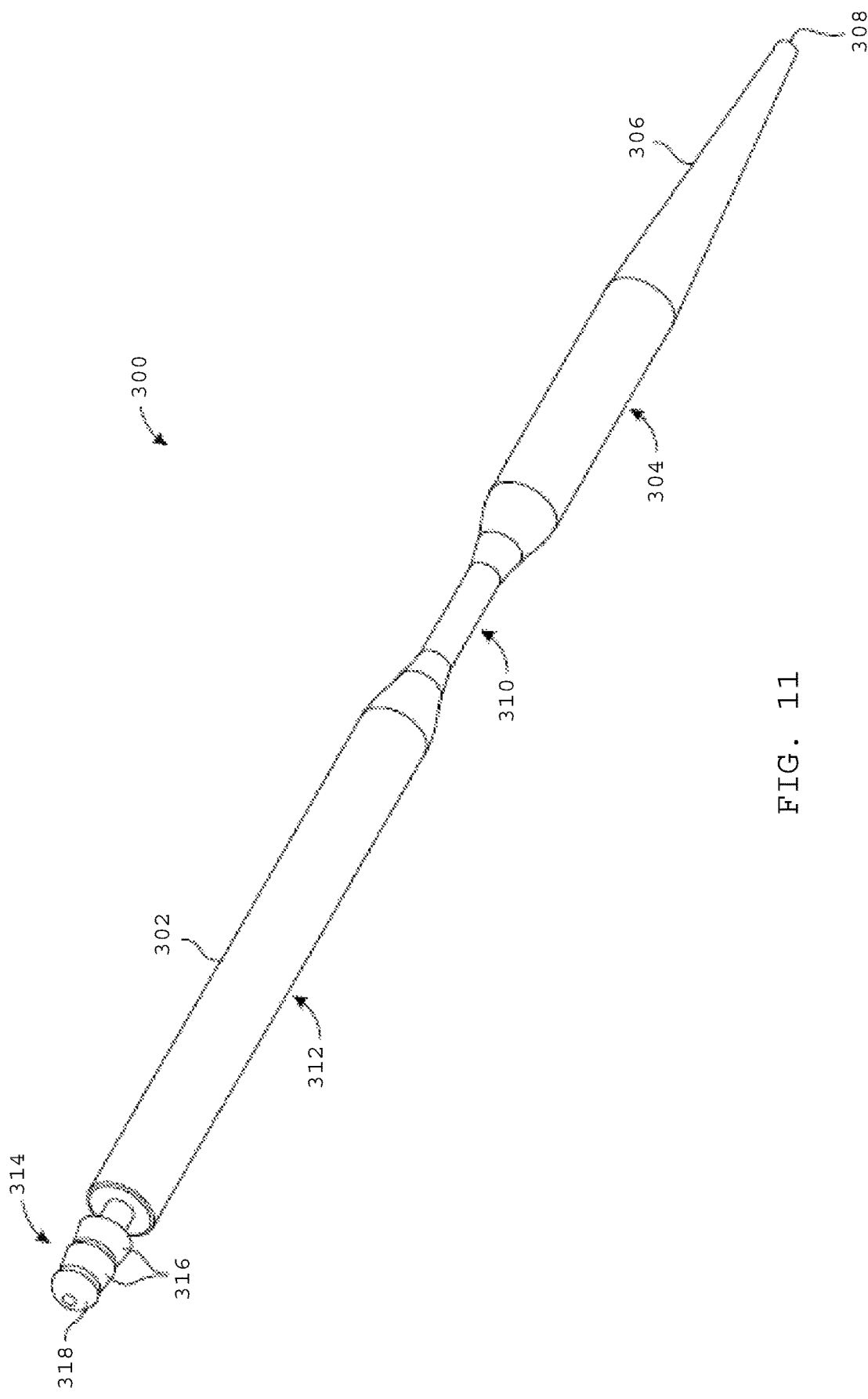
FIG. 11 is a perspective view of a trocar having a leading section including a tapered region that terminates at a blunt tip, a reduced diameter midsection, and a trailing section including a connector, in accordance with one embodiment of the present patent application.

Referring to FIG. 11, in one embodiment, a trocar 300 for conveying a wound drain catheter through tissue preferably includes an elongated shaft 302 having a leading section 304 with a tapered region 306 including a blunt tip 308 at a free end thereof, a reduced diameter midsection 310, and a trailing section 312 having a connector 314 including one or more annular ridges 316 and an end knob 318. In one embodiment, the trocar may be made of metal such as stainless steel, and more preferably 303 stainless steel.

Figure 12A:
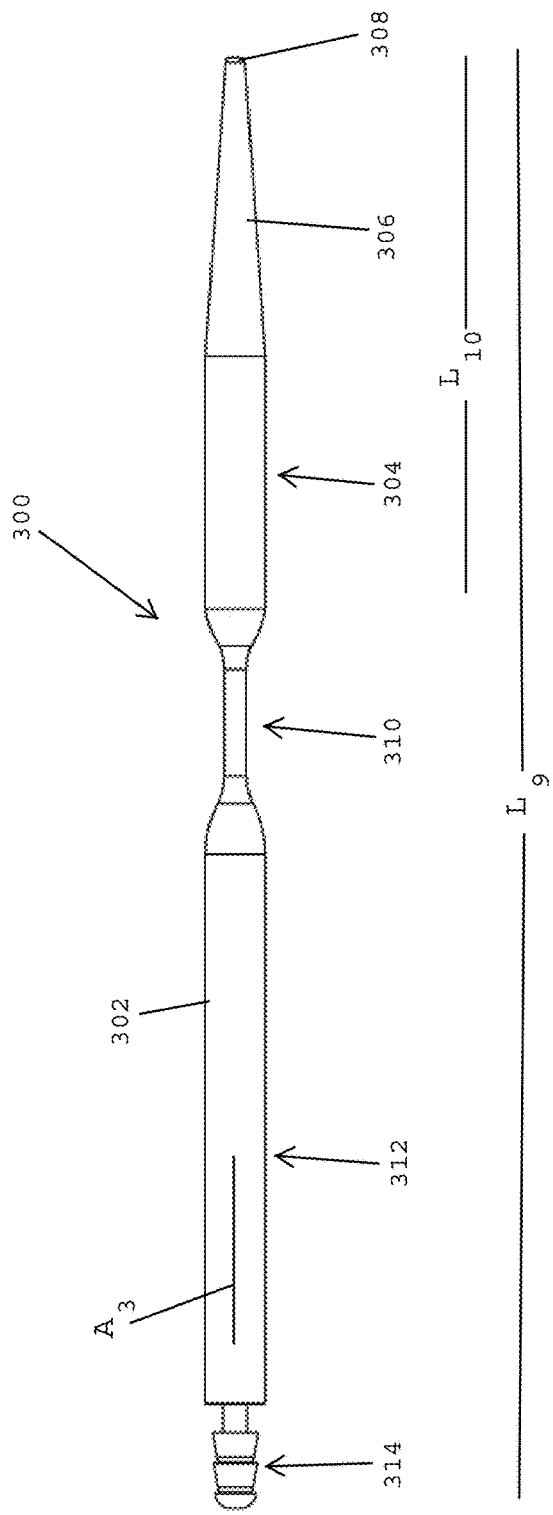
FIG. 12A is a side view of the trocar shown in FIG. 11.
Figure 12B:
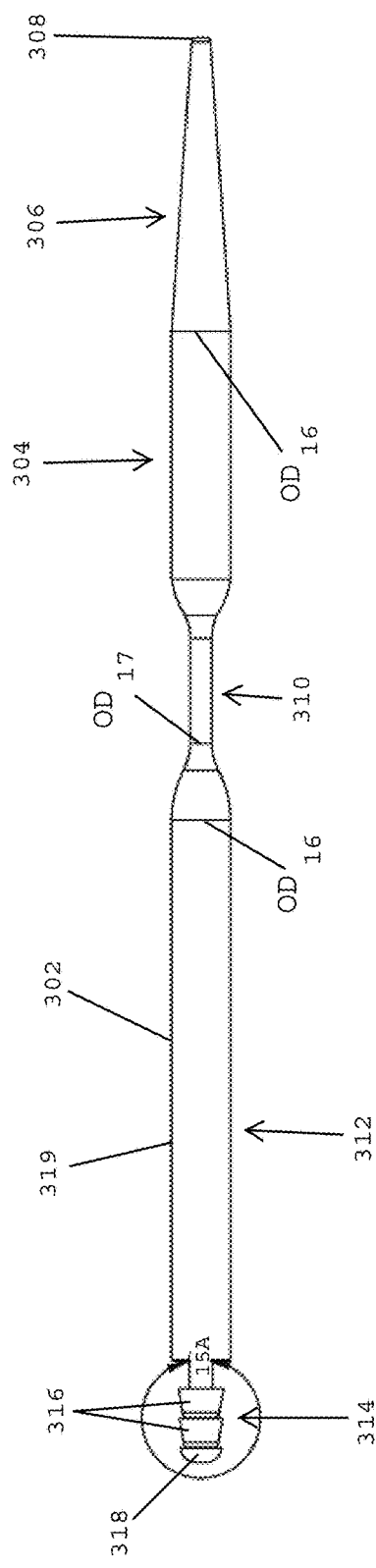
FIG. 12B is another side view of the trocar shown in FIG. 11.

Referring to FIGS. 12A and 12B, in one embodiment, the elongated shaft of the trocar 300 desirably has a longitudinal axis $A_3$ that extends along the length of the elongated shaft 302 from the connector 314 at the trailing section 312 of the shaft to the tapered region 306 at the leading section 304 of the shaft 302. In one embodiment, the elongated shaft 302 of the trocar has a length $L_9$ of about 5-7 inches and more preferably about 6 inches. In one embodiment, the leading section 304 of the elongated shaft 302 has a length $L_{10}$ of about 2-3 inches and more preferably about 2.50 inches.

In one embodiment, the trocar 300 has a French size of between Fr 10-Fr 24 and more preferably about Fr 19. In one embodiment, the elongated shaft 302 includes an outer surface 319 having a cylindrical shape. In one embodiment, the leading and trailing sections 304, 312 of the elongated shaft 302 define a first outer diameter $OD_{16}$ that is greater than a second outer diameter $OD_{17}$ of the reduced diameter midsection 310. In one embodiment, the larger first outer diameter $OD_{16}$ is about 0.250 inches and the smaller second outer diameter $OD_{17}$ is about 0.0925 inches. As will be described in more detail herein, the reduced diameter midsection 310 interconnects the trailing section 312 and the leading section 304 of the elongated shaft 302. The reduced diameter midsection 310 is more bendable than the leading and trailing sections of the shaft so that the leading section 304 of the shaft 302 may be bent at different angles relative to the trailing section 312 of the shaft 302. In one embodiment, all of the bending of the trocar desirably occurs within the reduced diameter midsection 310 region. In one embodiment, as the leading section 304 is angulated relative to the trailing section 312, the leading and trailing sections preferably maintain a straight configuration.

Referring to FIG. 12B, in one embodiment, the connector 314 located at the trailing end of the trailing section 312 of the elongated shaft 302 desirably includes one or more annular ridges 316 that are adapted to engage with an inner surface of a wound drain catheter for connecting the wound drain catheter to the trailing section 312 of the trocar 300. The connector 314 desirably includes an end knob 318 that is inserted into an opening or conduit accessible at an end of a wound drain catheter for connecting a wound drain catheter to the trailing section of the trocar. In one embodiment, the wound drain catheter preferably has an outer diameter that matches the French size of the trocar.

Figure 13A:
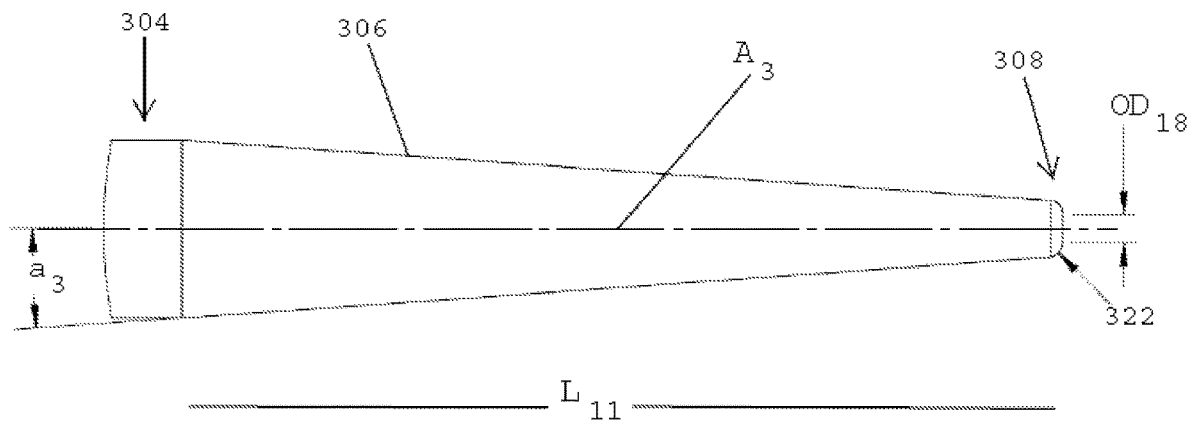
FIG. 13A is a side view of the tapered region and the blunt tip at the leading end of the trocar shown in FIG. 11.
Figure 13B:
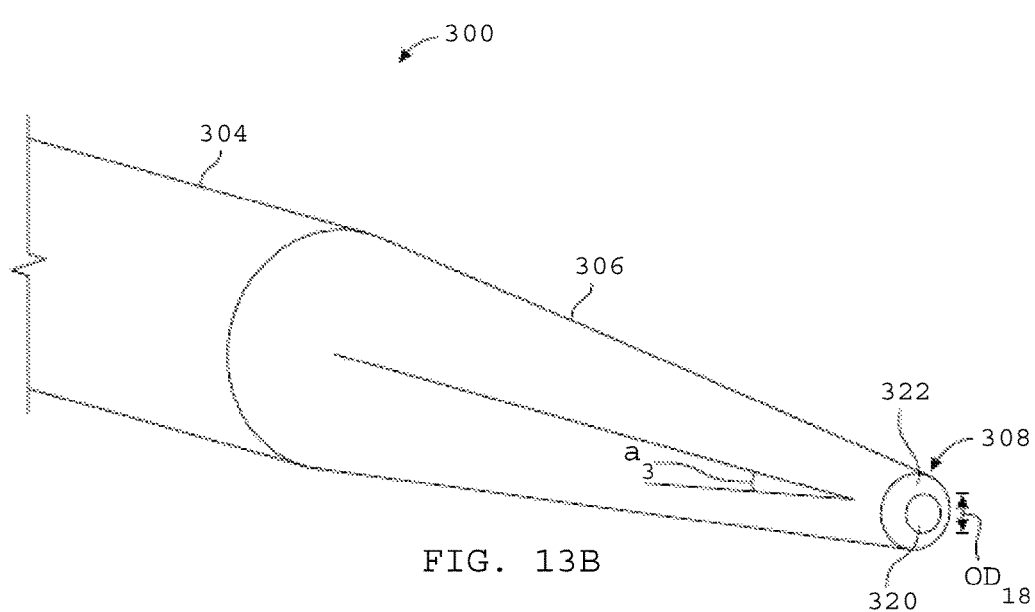
FIG. 13B is a perspective view of the tapered region and the blunt tip at the leading end of the trocar shown in FIG. 11.
Figure 13C:
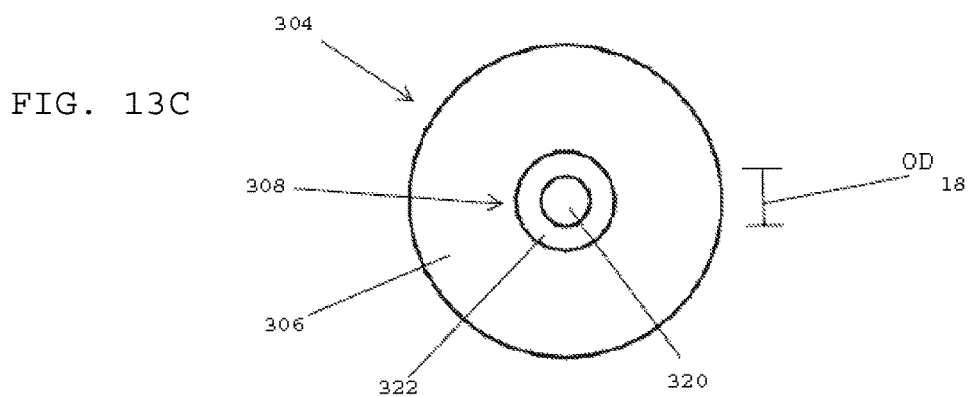
FIG. 13C is an end view of the tapered section and the blunt tip at the leading end of the trocar shown in FIG. 11.

Referring to FIGS. 13A-13C, in one embodiment, the leading section 304 (FIG. 11) of the elongated shaft of the trocar preferably includes the tapered region 306 that tapers inwardly to the blunt tip 308. In one embodiment, the blunt tip 308 preferably has a flat end surface 320 having an outer diameter $OD_{10}$ of about 0.040 inches. The blunt tip 308 preferably includes a curved surface 322, such as a convexly curved surface, that extends between the outer perimeter of the flat end surface 320 and the sloping sidewalls of the tapered region 306 of the leading section 304 of the trocar 300. In one embodiment, the curved surface 322 has a radius $R_3$ of about 0.020 inches.

In one embodiment, the tapered region 306 of the leading section 304 of the elongated shaft tapers outwardly from the blunt tip 308. In one embodiment, the tapered region 306 of the leading section 304 of the trocar has a length $L_{11}$ of about 0.741 inches. In one embodiment, the sloping outer surface of the tapered region 306 defines an angle $\alpha_3$ of about three-five degrees and more preferably about four degrees (4°) relative to the longitudinal axis $A_3$ of the elongated shaft of the trocar 300.

Figure 14A:
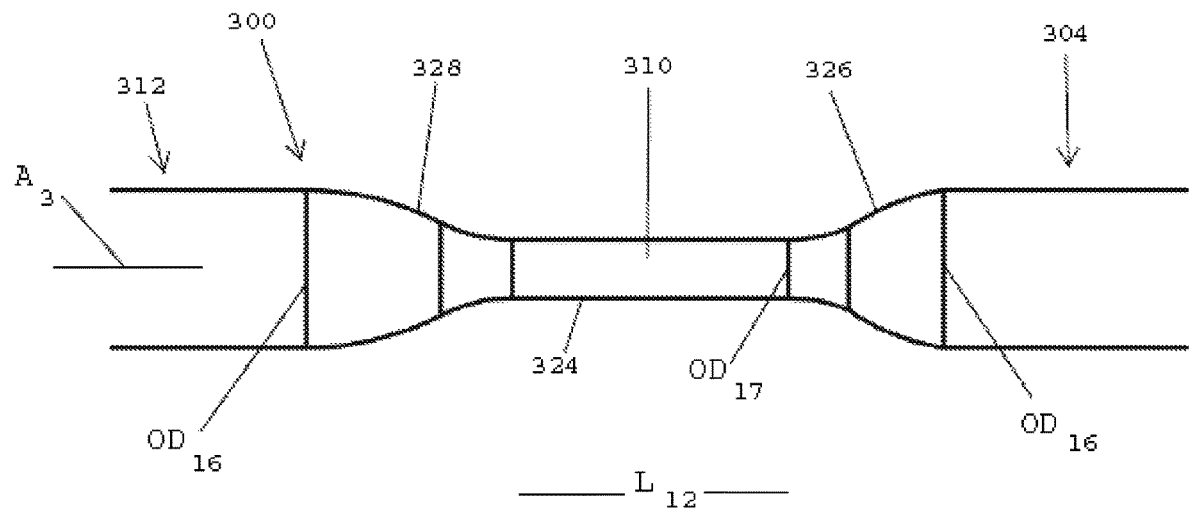
FIG. 14A is a side view of the reduced diameter midsection of the trocar shown in FIG. 11.
Figure 14B:
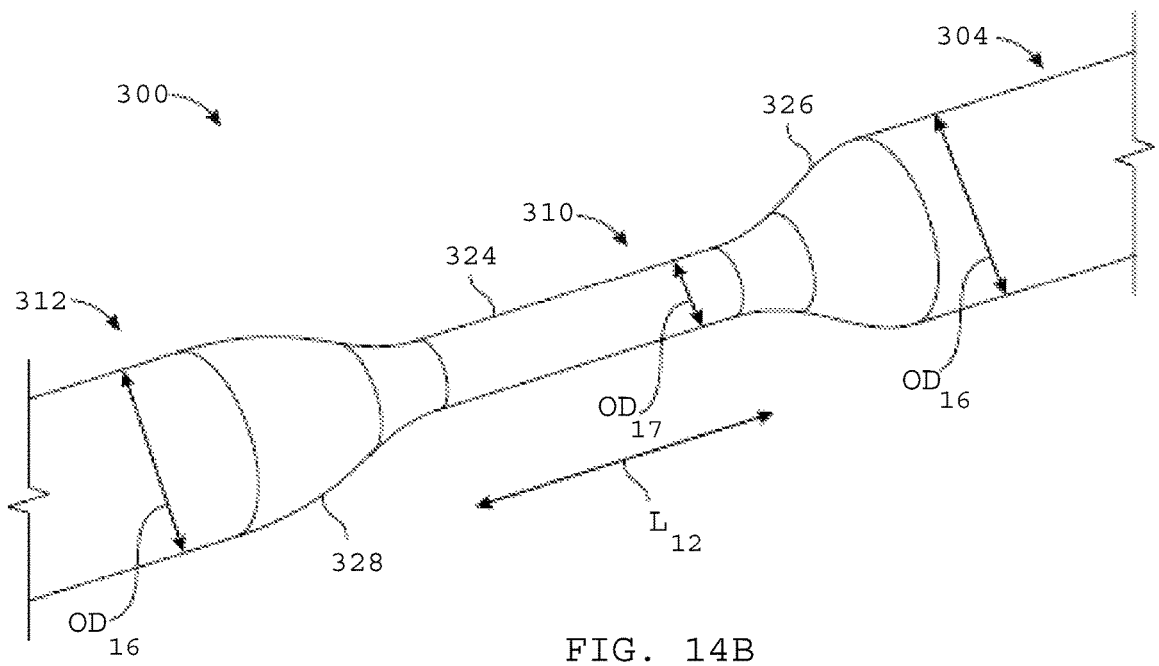
FIG. 14B is a perspective view of the reduced diameter midsection of the trocar shown in FIG. 11.

Referring to FIGS. 14A and 14B, in one embodiment, the reduced diameter midsection 310 of the trocar 300 desirably has an outer cylindrical surface 324 that defines the second outer diameter $OD_{17}$ of about 0.0925 inches, which is less than the respective first outer diameters $OD_{16}$ of about 0.250 inches of the leading and trailing sections 304, 312 of the elongated shaft of the trocar 300. In one embodiment, a leading end of the reduced diameter midsection 310 preferably has a first shoulder 326 that slopes or tapers outwardly between the second outer diameter $OD_{17}$ of the reduced diameter midsection 310 and the larger, first outer diameter $OD_{16}$ of the leading section 304 of the elongated shaft of the trocar. In one embodiment, a trailing end of the reduced diameter midsection 310 has a second shoulder 328 that slopes or tapers outwardly between the smaller, second outer diameter $OD_{17}$ of the reduced diameter midsection 310 and the larger, second outer diameter $OD_{16}$ of the trailing section 312 of the elongated shaft 302. In one embodiment, the reduced diameter midsection 310 of the trocar 200 has a length of $L_{12}$ of about 0.40-0.50 inches and more preferably about 0.440 inches.

Figure 15A:
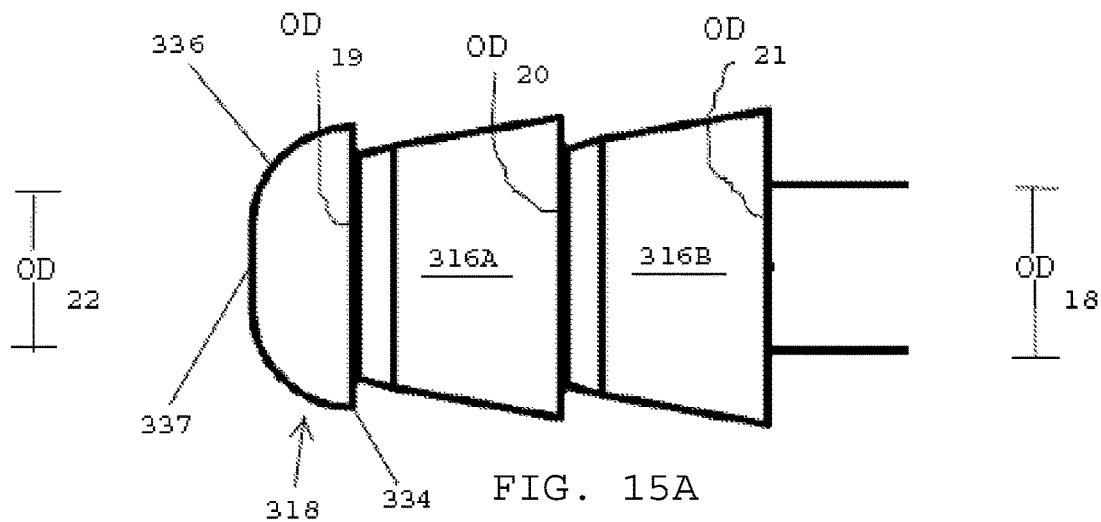
FIG. 15A is a side view of the connector at the trailing end of the trocar shown in FIG. 11.
Figure 15B:
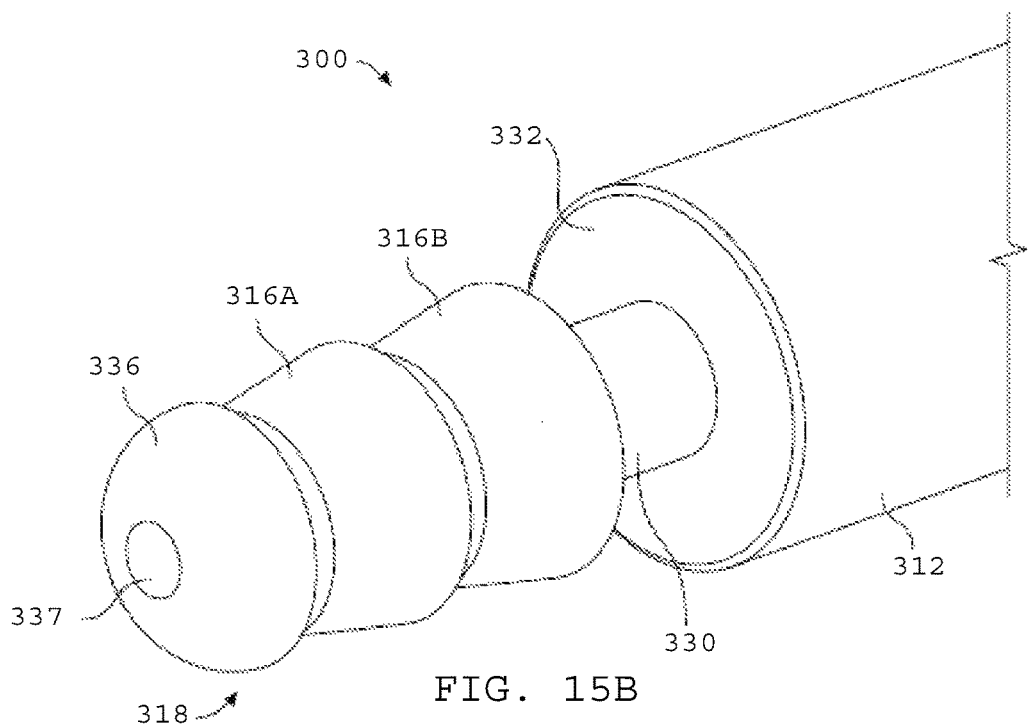
FIG. 15B is a perspective view of the connector at the trailing end of the trocar shown in FIG. 11.
Figure 15C:
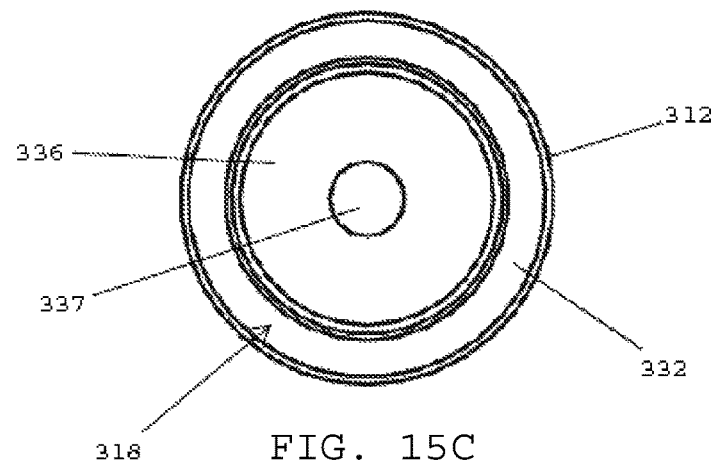
FIG. 15C is an end view of the connector at the trailing end of the trocar shown in FIG. 11.

Referring to FIGS. 15A-15C, in one embodiment, the connector 314 at the trailing end of the trailing section 312 (FIG. 11) of the trocar desirably includes annular ridges 316A, 316B that project outwardly from a stem 330 that is connected with an end face 332 (FIG. 15B) of the trailing section 312 of the elongated shaft of the trocar 300. In one embodiment, the stem 330 has an outer diameter $OD_{18}$ (FIG. 15A) of about 0.100 inches. In one embodiment, the end knob 318 has a base 334 defining the largest diameter section of the end knob. In one embodiment, the base 334 defines an outer diameter $OD_{19}$ (FIG. 15A) of about 0.170 inches. In one embodiment, the first ridge 316A defines an outer diameter $OD_{20}$ (FIG. 15A) of about 0.182 inches. In one embodiment, the second ridge 316B defines an outer diameter $OD_{21}$ (FIG. 15A) of about 0.190 inches. Thus, in one embodiment, the respective outer diameters of the end knob 318 and the first and second annular ridges 316A, 316B increase in series between the end knob 318 and the second annular ridge 316B. For example, in one embodiment, the first annular ridge has a larger outer diameter than the end knob, and the second annular ridge has a larger outer diameter than the first annular ridge. In one embodiment, the end knob 318 preferably has a curved surface 336 and a flat end surface 337 having an outer diameter $OD_{22}$ of about 0.100 inches.

Figure 16:
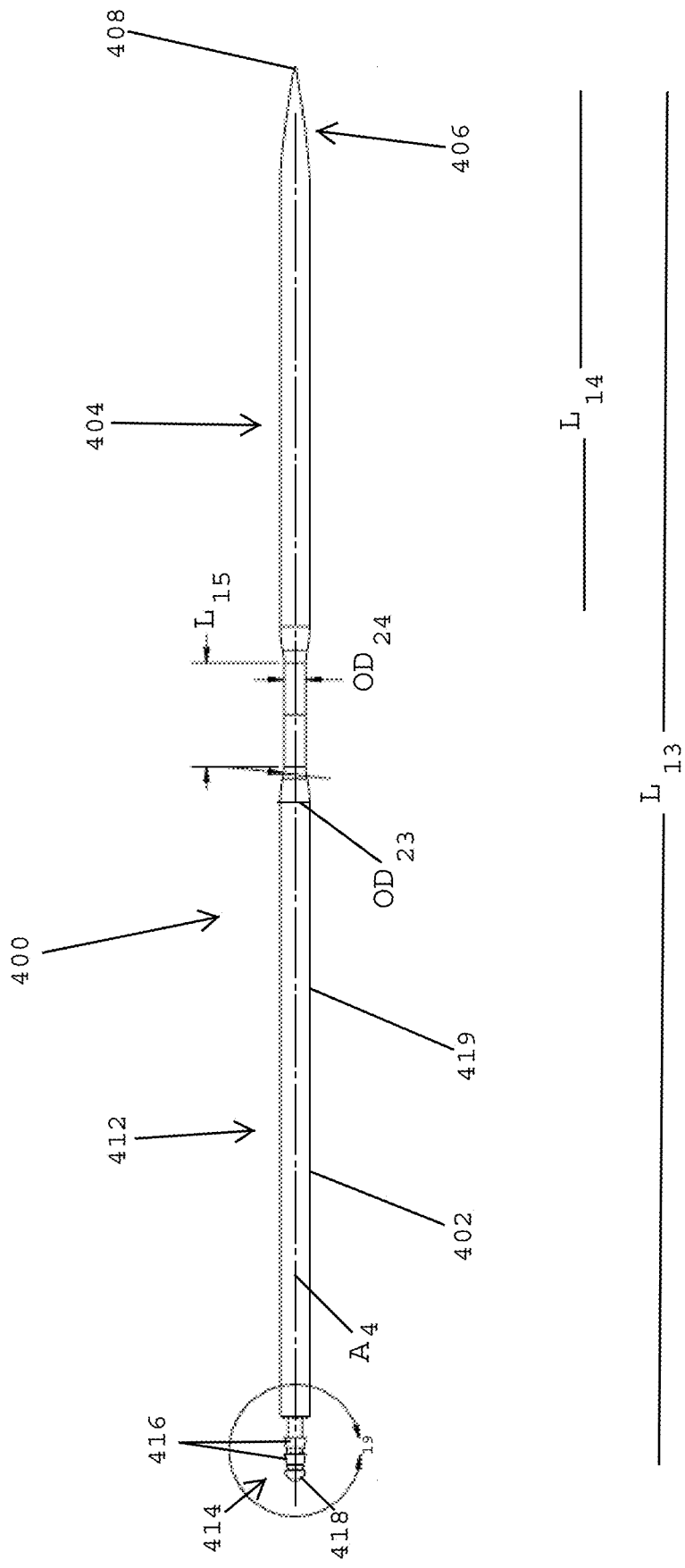
FIG. 16 is a side view of a trocar having a tapered leading section with a sharpened tip, a reduced diameter midsection, and a trailing section having a connector, in accordance with yet another embodiment of the present patent application.

Referring to FIG. 16, in one embodiment, a trocar 400 for conveying a wound drain catheter through tissue preferably includes an elongated shaft 402 having a leading section 404 with a tapered region 406 including a sharpened tip 408 at a free end thereof, a reduced diameter midsection 410, and a trailing section 412 having a connector 414 including one or more annular ridges 416 and an end knob 418. In one embodiment, the trocar 400 may be made of metal such as stainless steel, and more preferably 303 stainless steel.

In one embodiment, the elongated shaft of the trocar 400 desirably has a longitudinal axis $A_4$ that extends along the length thereof from the connector 414 at the trailing section 412 of the shaft to the sharpened tip 408 at the leading section 404 of the shaft 402. In one embodiment, the elongated shaft 402 of the trocar has a length $L_{13}$ of about 5-7 inches and more preferably about 6 inches. In one embodiment, the leading section 404 of the elongated shaft 402 has a length $L_{14}$ of about 2-3 inches and more preferably about 2.50 inches.

In one embodiment, the trocar 400 has a French size of between Fr 10-Fr 24 and more preferably Fr 10, Fr 15, or Fr 19. In one embodiment, the elongated shaft 402 preferably includes an outer surface 419 having a cylindrical shape. In one embodiment, the leading and trailing sections 404, 412 of the elongated shaft 402 define a first outer diameter $OD_{23}$ that is greater than a second outer diameter $OD_{24}$ of the reduced diameter midsection 410. In one embodiment, the larger, first outer diameter $OD_{23}$ is about 0.125 inches and the smaller, second outer diameter $OD_{24}$ is about 0.0925 inches. As will be described in more detail herein, the reduced diameter midsection 410 interconnects the trailing section 412 and the leading section 404 of the elongated shaft 402. The reduced diameter midsection 410 is more flexible and/or bendable than the leading and trailing sections of the shaft so that the leading section 404 of the shaft 402 may be bent at different angles relative to the trailing section 412 of the shaft 402. In one embodiment, all of the bending of the trocar desirably occurs within the reduced diameter midsection 410 region. In one embodiment, as the leading section 404 is angulated relative to the trailing section 412 by bending the reduced diameter midsection 410, the leading and trailing sections preferably maintain a straight configuration.

In one embodiment, the connector 414 located at the trailing end of the trailing section 412 of the elongated shaft 402 desirably includes one or more annular ridges 416 that are adapted to engage with an inner surface of a wound drain catheter for connecting the wound drain catheter to the trailing section 412 of the trocar 400. The connector 414 desirably includes an end knob 418 that is inserted into an opening or conduit accessible at an end of a wound drain catheter for connecting a wound drain catheter to the trailing section of the trocar.

Figure 17:
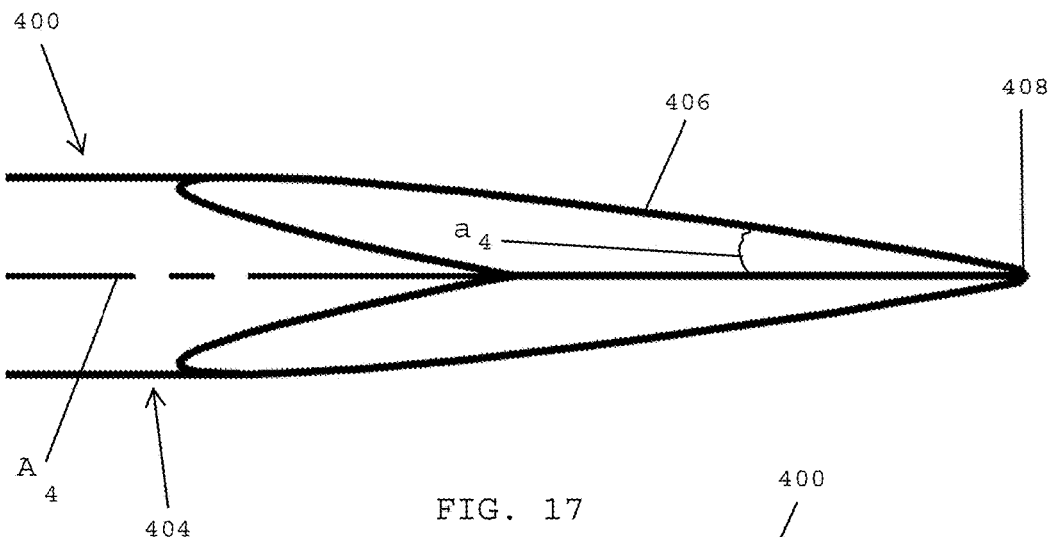
FIG. 17 is a side view of the tapered leading section with the sharpened tip of the trocar shown in FIG. 16.

Referring to FIG. 17, in one embodiment, the leading section 404 (FIG. 16) of the elongated shaft of the trocar preferably includes the tapered region 406 that tapers inwardly to the sharpened tip 408. In one embodiment, the tapered region 406 of the leading section 404 tapers outwardly from the sharpened tip 408. In one embodiment, the sloping outer surface of the tapered region 406 defines an angle $\alpha_4$ of about eight degrees (8°) relative to the longitudinal axis $A_4$ of the elongated shaft of the trocar 400.

Figure 18:
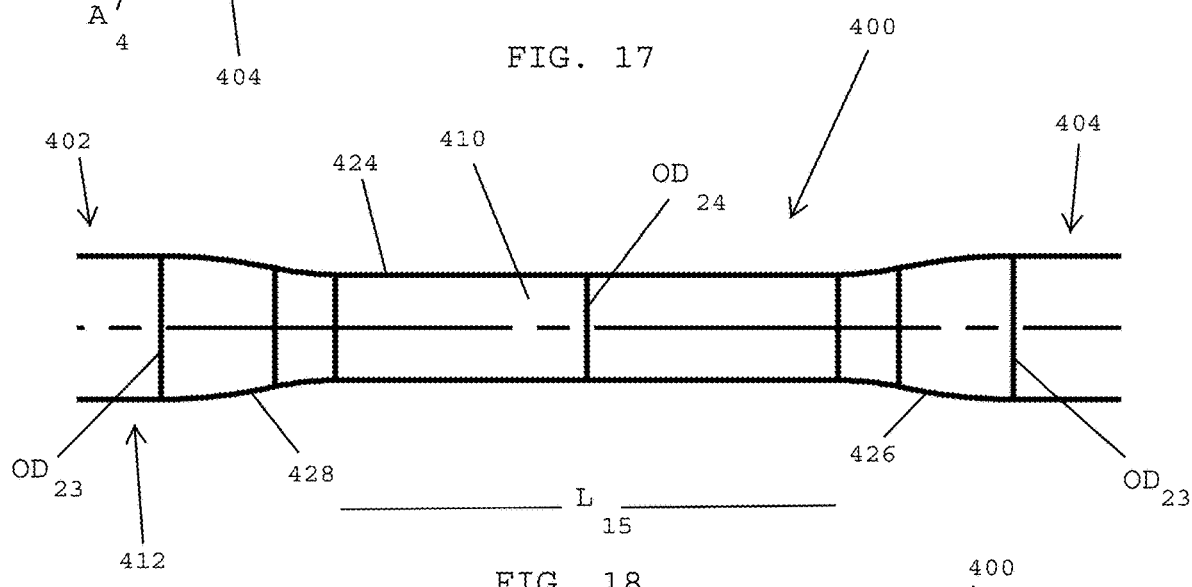
FIG. 18 is a side view of the reduced diameter midsection of the trocar shown in FIG. 16.

Referring to FIG. 18, in one embodiment, the reduced diameter midsection 410 of the elongated shaft 402 of the trocar 400 desirably has an outer cylindrical surface 424 that defines the second outer diameter $OD_{24}$ of about 0.0925 inches, which is less than the respective first outer diameters $OD_{23}$ of about 0.125 inches of the leading and trailing sections 404, 412 of the elongated shaft 402 of the trocar 400. The leading end of the reduced diameter midsection 410 preferably has a first shoulder 426 that slopes or tapers outwardly between the second outer diameter $OD_{24}$ of the reduced diameter midsection 310 and the larger, first outer diameter $OD_{23}$ of the leading section 404 of the elongated shaft of the trocar. In addition, the trailing end of the reduced diameter midsection 410 has a second shoulder 428 that slopes or tapers outwardly between the smaller, second outer diameter $OD_{24}$ of the reduced diameter midsection 410 and the larger, second outer diameter $OD_{23}$ of the trailing section 412 of the elongated shaft 402. In one embodiment, the reduced diameter midsection 410 of the trocar 400 has a length of $L_{15}$ of about 0.40-0.50 inches and more preferably about 0.440 inches.

Figure 19:
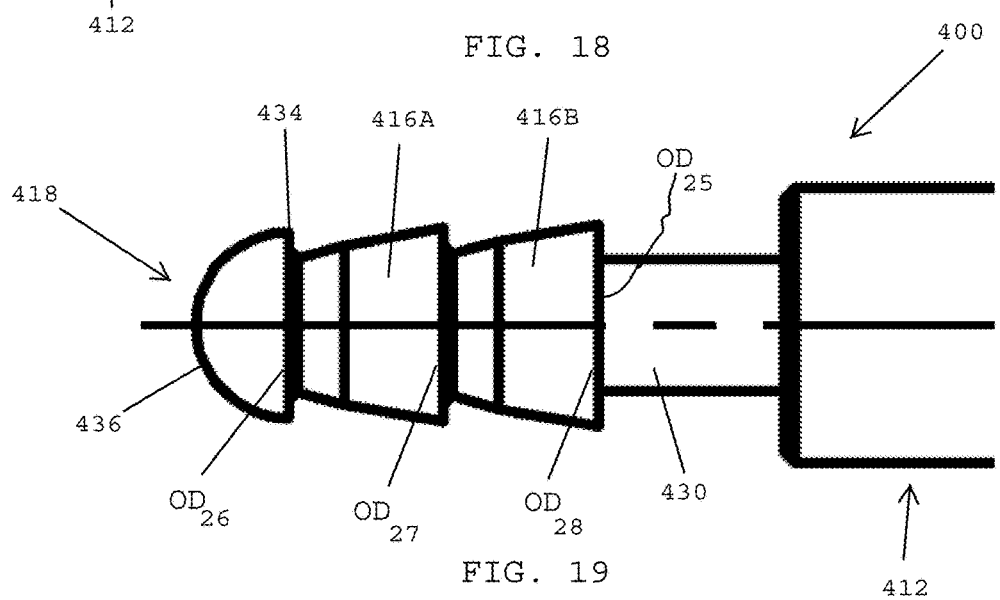
FIG. 19 shows is a side view of the connector at the trailing end of the trocar shown in FIG. 16.

Referring to FIG. 19, in one embodiment, the connector 414 at the trailing section 412 (FIG. 16) of the trocar 400 desirably includes annular ridges 416A, 416B that project outwardly from a stem 430 that is connected with an end face 432 of the trailing section 412 of the elongated shaft of the trocar 400. In one embodiment, the stem 430 has an outer diameter $OD_{25}$ of about 0.060 inches. In one embodiment, the end knob 418 has a base 434 defining the largest diameter section of the end knob. In one embodiment, the base 434 defines an outer diameter $OD_{26}$ of about 0.085 inches. In one embodiment, the first ridge 416A defines an outer diameter $OD_{27}$ of about 0.088 inches. In one embodiment, the second ridge 416B defines an outer diameter $OD_{28}$ of about 0.092 inches. Thus, in one embodiment, the respective outer diameters of the end knob 418 and the first and second annular ridges 416A, 416B increase in series between the end knob 418 and the second annular ridge 416B. In one embodiment, the end knob 418 preferably has a curved surface 436.

Figure 20A:
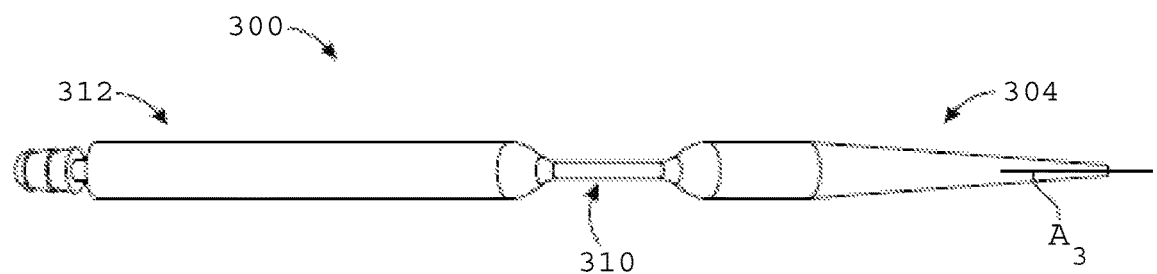
FIG. 20A is a side view of the trocar shown in FIG. 11 in a straight configuration.

FIGS. 20A-20F illustrate the bendable trocar 300 shown and described above in FIGS. 11-15C being bent into different angular configurations. Referring to FIG. 20A, in one embodiment, the trocar 300 has the reduced diameter midsection 310 that enables the leading section 304 and the trailing section 312 of the trocar to be angulated relative to one another. In FIG. 20A, the trocar 300 is in a straight configuration so that the leading section 304, the reduced diameter midsection 310, and the trailing section 312 all extend along a common axis $A_3$.

Figure 20B:
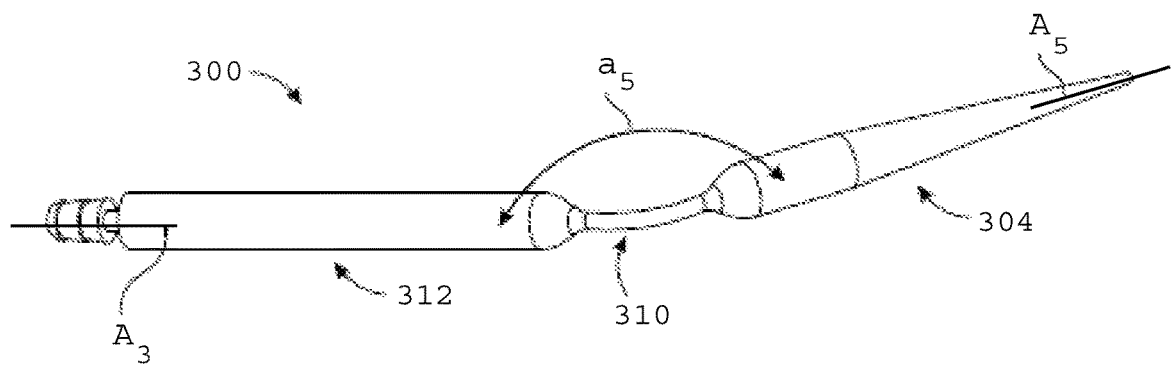
FIG. 20B is a side view of the trocar shown in FIG. 20A in a first bent configuration, in accordance with one embodiment of the present patent application.

Referring to FIG. 20B, in one embodiment, the trocar 300 is bent at the reduced diameter midsection 310 so that the leading section 304 of the elongated shaft 302 extends along an axis $A_5$ and the trailing section 312 of the elongated axis extends along the axis $A_3$ to define an angle $\alpha_5$ of about 30 degrees.

Figure 20C:
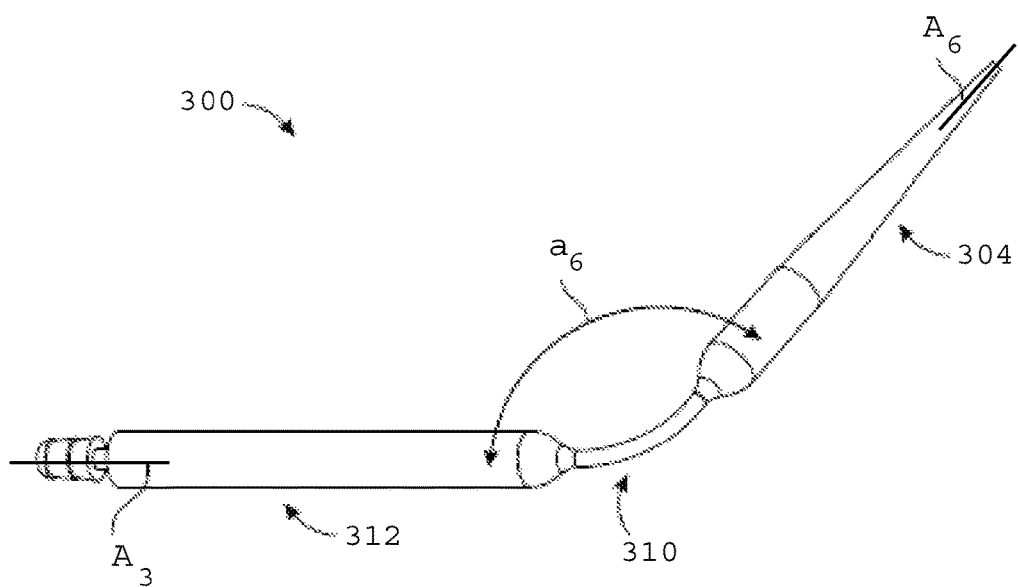
FIG. 20C is a side view of the trocar shown in FIG. 20A in a second bent configuration, in accordance with one embodiment of the present patent application.

Referring to FIG. 20C, in one embodiment, the trocar 300 is further bent at the reduced diameter midsection 310 so that the leading section 304 of the elongated shaft 302 extends along an axis $A_6$ and the trailing section 312 of the elongated axis extends along the axis $A_3$ to define an angle $\alpha_6$ of about 45 degrees.

Figure 20D:
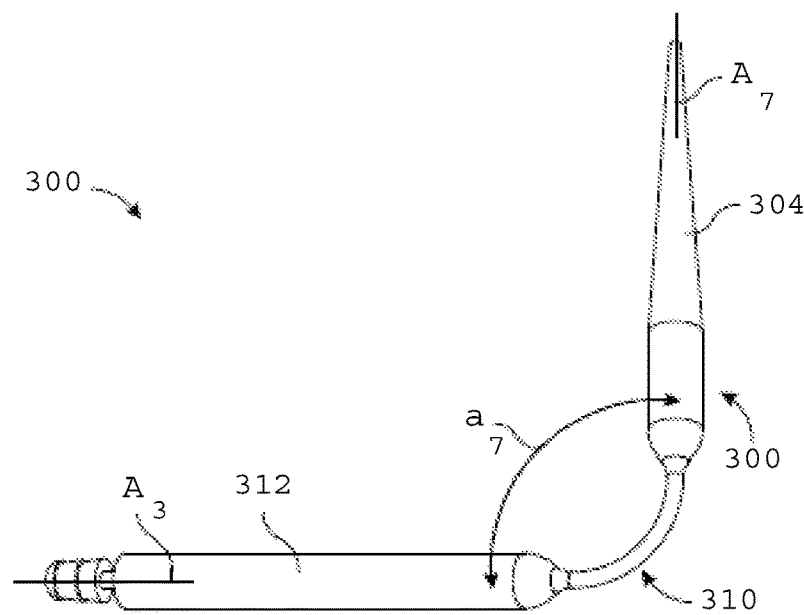
FIG. 20D is a side view of the trocar shown in FIG. 20A in a third bent configuration, in accordance with one embodiment of the present patent application.

Referring to FIG. 20D, in one embodiment, the trocar 300 is further bent at the reduced diameter midsection 310 so that the leading section 304 of the elongated shaft 302 extends along an axis $A_7$ and the trailing section 312 of the elongated axis extends along the axis $A_3$ to define an angle $\alpha_7$ of about 90 degrees.

Figure 20E:
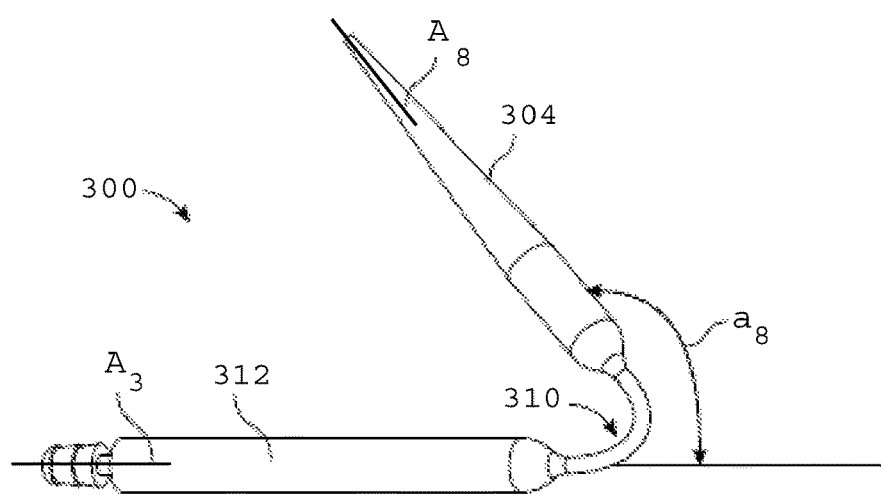
FIG. 20E is a side view of the trocar shown in FIG. 20A in a fourth bent configuration, in accordance with one embodiment of the present patent application.

Referring to FIG. 20E, in one embodiment, the trocar 300 is still further bent at the reduced diameter midsection 310 so that the leading section 304 of the elongated shaft 302 extends along an axis $A_8$ and the trailing section 312 of the elongated axis extends along the axis $A_3$ to define an angle $\alpha_8$ of about 120 degrees.

Figure 20F:
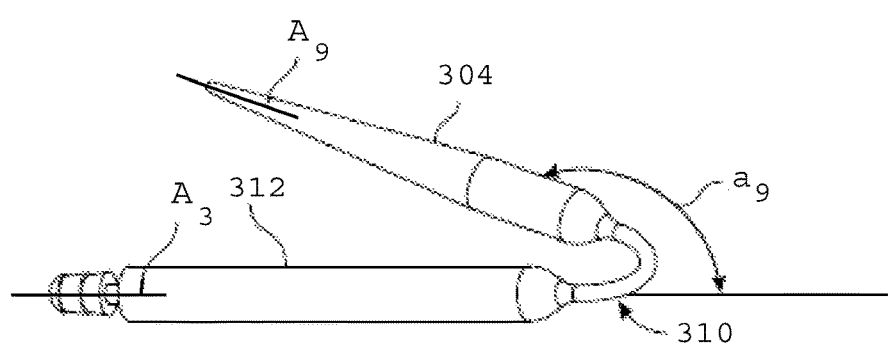
FIG. 20F is a side view of the trocar shown in FIG. 20A in a fifth bent configuration, in accordance with one embodiment of the present patent application.

Referring to FIG. 20F, in one embodiment, the trocar 300 is yet further bent at the reduced diameter midsection 310 so that the leading section 304 of the elongated shaft 302 extends along an axis $A_9$ and the trailing section 312 of the elongated axis extends along the axis $A_3$ to define an angle $\alpha_9$ of about 135 degrees.

Figure 21A:
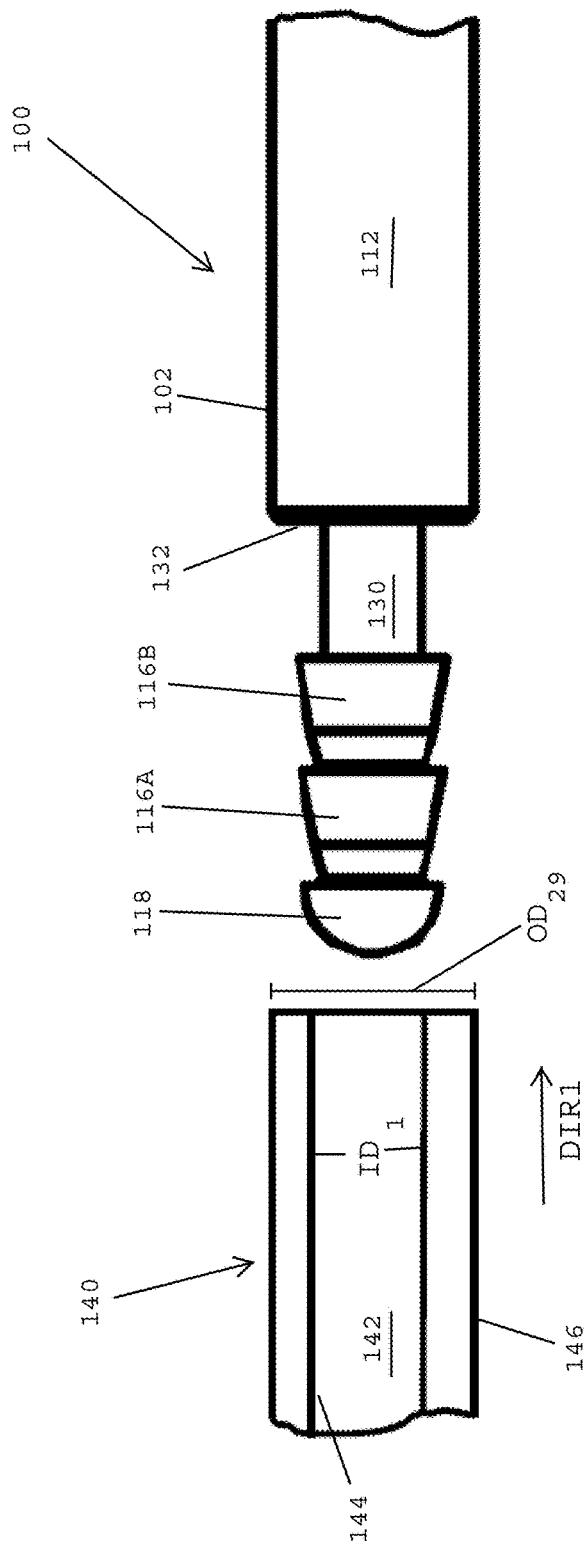
FIG. 21A shows a first step of a method for securing a wound drain catheter to a connector at a trailing end of a trocar, in accordance with one embodiment of the present patent application.
Figure 21B:
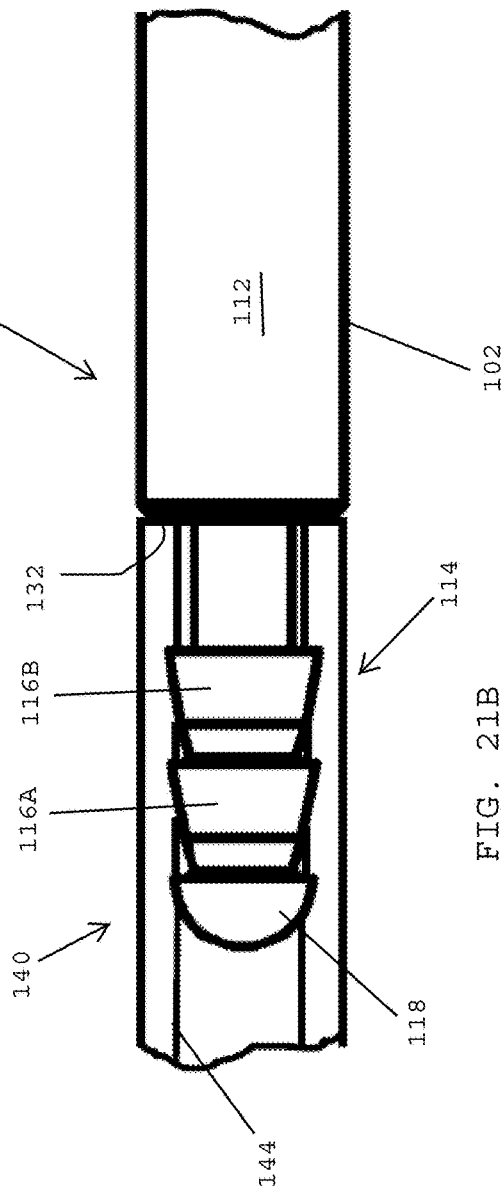
FIG. 21B shows a second step of a method for securing a wound drain catheter to a connector at a trailing end of a trocar, in accordance with one embodiment of the present patent application.

Referring to FIGS. 21A and 21B, in one embodiment, a wound drain catheter 140 is secured to the connector 114 extending from the trailing section 112 of the trocar 100 (FIG. 1). In one embodiment, the wound drain catheter 140 preferably has a central conduit 142 surrounded by an inner wall 144 of the catheter, which defines an inner diameter $ID_1$ that is less than the outer diameters of the respective end knob 118 and annular ridges 116A, 116B. In one embodiment, the inner diameter $ID_1$ is less than 0.085 inches. In one embodiment, the wound drain catheter has an outer diameter that matches the French size of the trocar 100. In one embodiment, the wound drain catheter 140 preferably has an outer surface 146 defining an outer diameter $OD_{29}$ that is substantially similar with the outer diameter $OD_1$ (FIG. 2A) of the trailing section 112 of the catheter 100. In one embodiment, the outer diameter $OD_{29}$ of the wound drain catheter and the outer diameter $OD_1$ of the trailing section 112 of the elongated shaft 102 of the catheter 100 is about 0.125 inches.

In one embodiment, in order to attach the wound drain catheter 140 with the trailing section 112 of the catheter 100, the opening in the catheter defined by the conduit 142 is passed in series over the end knob 118 and the first and second annular ridges 116A, 116B of the connector 114 until the end of the catheter abuts against the end face 132 at the trailing end of the trailing section 112 of the elongated shaft. As shown in FIG. 21B, the knob 118 and the annular ridges 116A, 116B have respective outer diameters that are slightly larger than the inner diameter $ID_1$ defined by the inner wall 144 of the wound drain catheter 140 for forming a secure attachment between the wound drain catheter and the connector 114 at the trailing end of the trailing section 112 of the trocar 100.

Figure 22:
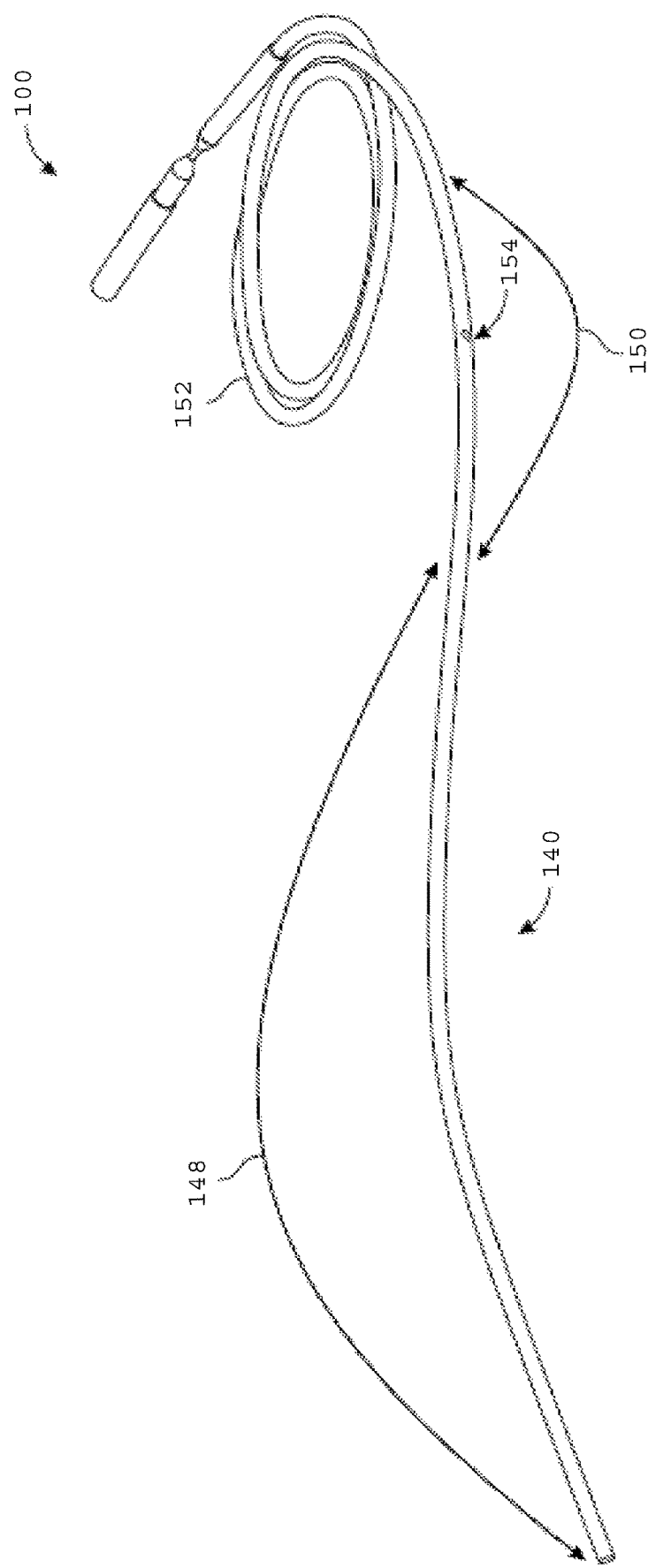
FIG. 22 shows a perspective view of a system for draining a wound including a wound drain catheter having a flute section, a transition section, and an extension section having a distal end secured to a trailing end of a trocar, in accordance with one embodiment of the present patent application.

Referring to FIG. 22, in one embodiment, a wound drain catheter 140 (FIGS. 21A, 21B) may be secured to the trocar 100. The wound drain catheter 140 preferably includes a flute section 148, a transition section 150, and an extension section 152. A midpoint of the transition section 150 may be defined by indicia 154, such as a black dot, located on an outer surface of the transition section 150 of the wound drain catheter. In one embodiment, a free end of the extension section 152 may be secured to a connector at a trailing section of a trocar as shown and described above in FIGS. 21A and 21B.

Referring to FIG. 23, in one embodiment, the extension section 152 of the wound drain catheter 140 preferably defines an open structure for enabling fluid to readily pass therethrough.

Referring to FIG. 24, in one embodiment, the transition section 150 of the wound drain catheter 140 preferably has cruciform shaped struts 156 that prevent the outer wall of the transition section of the wound drain catheter from collapsing inwardly due to external force being exerted upon the outer wall of the wound drain catheter.

Referring to FIG. 25, in one embodiment, a drain 160 may be coupled with a wound drain catheter. In one embodiment, the drain 160 may incorporate one or more of the structural features disclosed in U.S. Pat. No. 4,398,910 to Blake et. al., the disclosure of which is hereby incorporated by reference herein.

Figure 26:
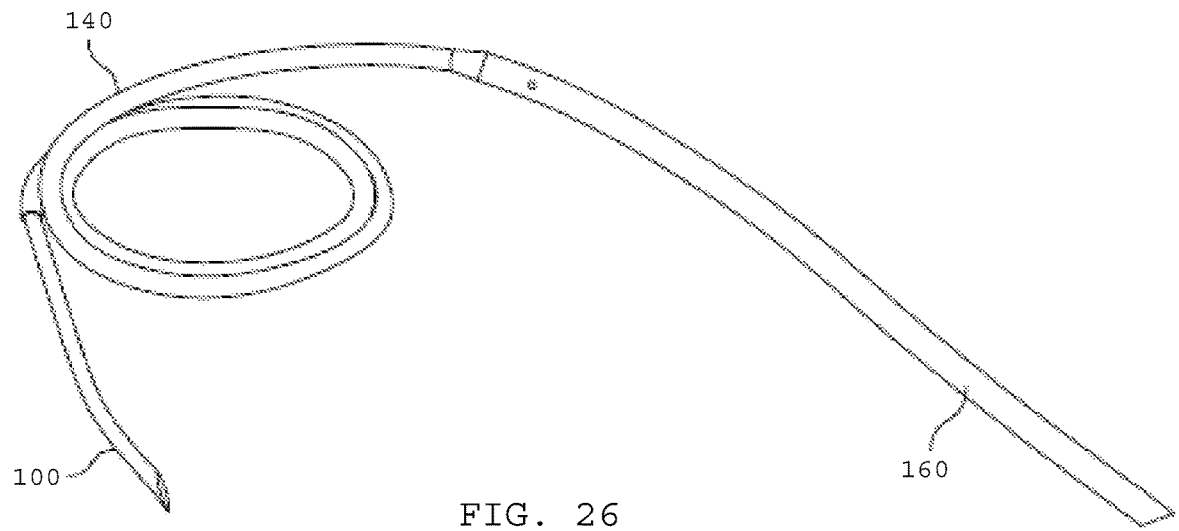
FIG. 26 shows a perspective view of a system for draining a wound including a trocar, a wound drain catheter, and a drain, in accordance with one embodiment of the present patent application.

Referring to FIG. 26, in one embodiment, a system for draining a wound may include a trocar 100 coupled with a leading end of a wound drain catheter 140, and a drain 160 coupled with a trailing end of the wound drain catheter 140. The drain 160 may have one or more of the structural features disclosed in the Blake '910 patent, the disclosure of which is hereby incorporated by reference herein.

Figure 27:
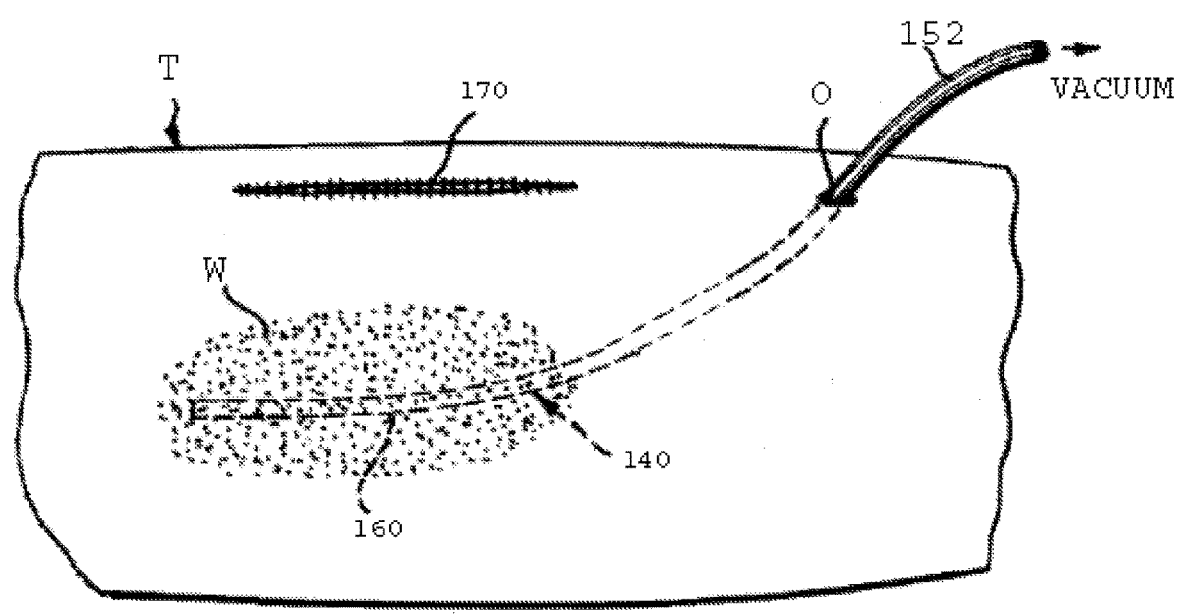
FIG. 27 shows a method of using a wound drain catheter for draining a wound, in accordance with one embodiment of the present patent application.

Referring to FIG. 27, in one embodiment, the trocar 100 (FIG. 22) is desirably advanced through tissue T to position the drain 160 at the location of a wound. The trocar (not shown) may be removed from the body by passing the trocar through an opening O in the tissue T. The extension section 152 of the wound drain catheter preferably extends out of the opening of the body for being coupled with vacuum that draws fluid from the wound for being discharged via the wound drain catheter 140.

In one embodiment, the wound drain catheter 140 includes the drain 160 pre-connected to an end of the wound drain catheter. The drain 160 and the flute section 148 (FIG. 22) of the wound drain catheter are placed in a patient's body with the drain 160 in fluid communication with the wound W. Preferably, the extension section 152 of the wound drain catheter is connected to a sealed, sterilized suction device (FIG. 28) for drawing fluid through the wound drain catheter 140. In one embodiment, it is preferable that the extension section 152 of the wound drain catheter 140 exit the patient's body through an opening O formed in the patient's tissue T, adjacent to the wound W. In one embodiment, the wound drain catheter 140 preferably has a smooth exterior surface to permit the surface tissue surrounding the opening O to seal against the exterior of the catheter 140, and thus, prevent air from passing therebetween. The configuration shown in FIG. 27 preferably permits the wound W to be completely closed, as by sutures 170, and covered with a dressing (not shown) to form an aseptic barrier, thereby sealing the wound from the atmosphere. Thus, since the wound drain catheter 140 is only exposed to the sterile suction device, and not to the atmosphere, risk of infection is reduced.

Figure 28:
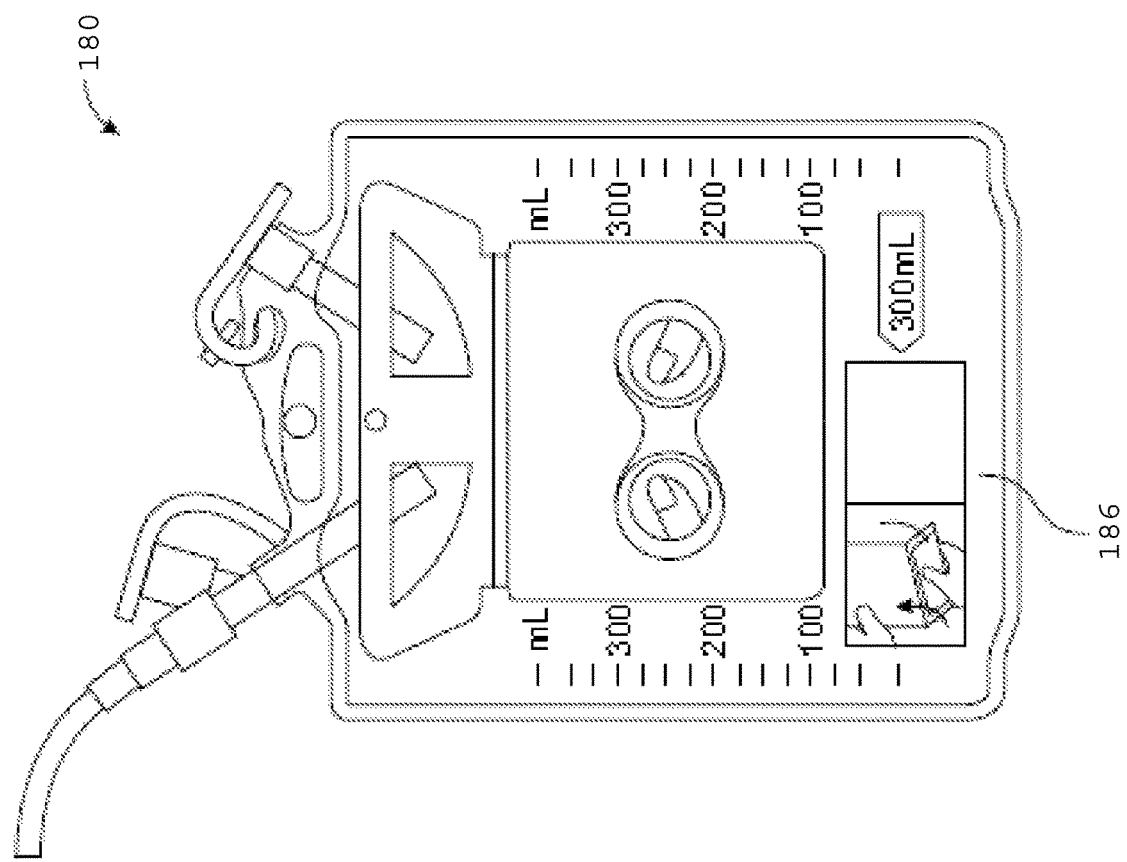
FIG. 28 shows a system for applying vacuum to an end of a wound drain catheter, in accordance with embodiment of the present patent application.
Figure 28:
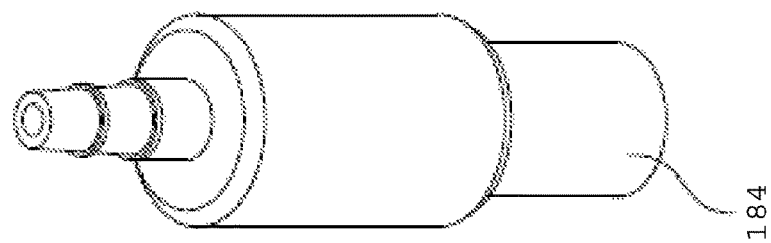
Figure 28:
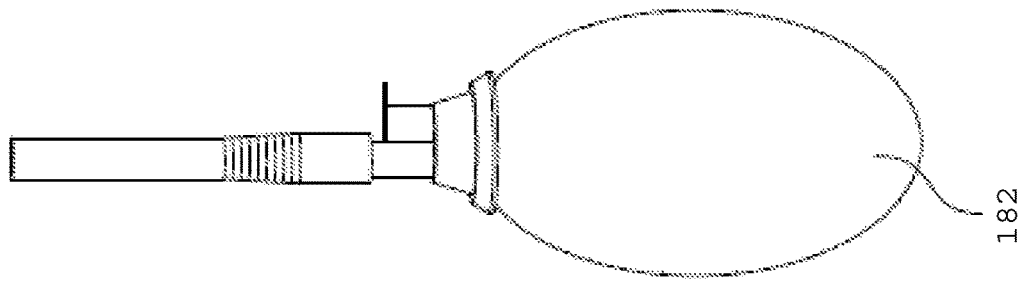

Referring to FIGS. 27 and 28, in one embodiment, a system 180 for generating suction or vacuum may be coupled with the extension section 152 of the wound drain catheter 140 that extends from the opening O (FIG. 27), for continuously drawing the fluid from the wound via the wound drain catheter. In one embodiment, the suction system 180 may include a bulb suction reservoir 182, a J-VAC drain adapter 184, and a J-VAC reservoir 186. In one embodiment, the system may include a metered container that is used for drawing a vacuum to permit the uniform removal of fluid from a wound.

In one embodiment, vacuum may be created using a flexible, compressible reservoir that draws a substantially constant vacuum to permit uniform removal of fluid from a wound via a wound drain catheter, such as the surgical fluid evacuator disclosed in U.S. Pat. No. 4,429,693 to Blake et al., the disclosure of which is hereby incorporated by reference herein.

The systems, devices and methods disclosed herein may be used for a wide variety of wound drainage applications located in any part of a human or mammal including but not limited to the upper gastrointestinal tract, the lower gastrointestinal tract, the heart, the circulatory system, the thoracic region, the breast region, joints, the spine, the cardiovascular system, the head, the face, the ear, the nose, and the throat.

While the foregoing is directed to embodiments of the present invention, other and further embodiments of the invention may be devised without departing from the basic scope thereof, which is only limited by the scope of the claims that follow. For example, the present invention contemplates that any of the features shown in any of the embodiments described herein, or incorporated by reference herein, may be incorporated with any of the features shown in any of the other embodiments described herein, or incorporated by reference herein, and still fall within the scope of the present invention.

What is claimed is:

1. A trocar comprising:
    an elongated shaft having a leading section, a trailing section, a reduced diameter midsection located between said leading and trailing sections, and a longitudinal axis extending from a leading end of said leading section to a trailing end of said trailing section of said elongated shaft;

said leading section of said elongated shaft having a tapered region that terminates at a blunt tip located at the leading end of said elongated shaft, wherein said tapered region includes a sloping surface having a conical shape that tapers away from the longitudinal axis of said elongated shaft, and wherein said sloping surface of said tapered region and the longitudinal axis of said elongated shaft define an angle of about three degrees (3°);

said trailing section of said elongated shaft having a connector located at the trailing end of said elongated shaft;

said leading and trailing sections of said elongated shaft having a first diameter and said reduced diameter midsection of said elongated shaft having a second diameter that is smaller than the first diameter for enabling said elongated shaft to be bent at said reduced diameter midsection.

2. The trocar as claimed in claim 1, wherein said elongated shaft comprises a material selected from the group consisting of metals, biocompatible metals, medical grade steel, stainless steel, 303 stainless steel, and polymers.

3. The trocar as claimed in claim 1, wherein said leading and trailing sections of said elongated shaft are relatively more rigid than said reduced diameter midsection of said elongated shaft, and wherein said reduced diameter midsection is more flexible than said leading and trailing sections.

4. The trocar as claimed in claim 1, wherein said elongated shaft includes an outer surface having a cylindrical shape.

5. The trocar as claimed in claim 1, wherein said blunt tip comprises:
a flat surface having an outer perimeter;
a convexly curved surface surrounding the outer perimeter of said flat surface and extending from the outer perimeter of said flat surface to said sloping surface of said tapered region.

6. The trocar as claimed in claim 5, wherein said flat surface of said blunt tip has an outer diameter of about 0.030-0.045 inches.

7. The trocar as claimed in claim 1, wherein the first diameter of said leading and trailing sections of said elongated shaft is about 0.125-0.250 inches, and the second diameter of said reduced diameter midsection is about 0.0875-0.0975 inches.

8. The trocar as claimed in claim 1, wherein said elongated shaft has a length of about 6 inches, said leading section of said elongated shaft has a length of about 2.75 inches, said tapered region of said leading section has a length of about 0.741 inches, and said reduced diameter midsection has a length of about 0.400-0.500 inches.

9. The trocar as claimed in claim 1, wherein said reduced diameter midsection is located midway between the leading and trailing ends of said elongated shaft.

10. The trocar as claimed in claim 1, wherein said connector comprises:
an end knob having a curved surface, said end knob having a base that defines the largest diameter section of said end knob;
a first annular ridge located between said end knob and an end face of said trailing section of said elongated shaft, wherein said first annular ridge has an outer diameter that is larger than the largest diameter section of said end knob.

11. The trocar as claimed in claim 10, wherein said connector further comprises a second ridge located between said first ridge and the end face of said trailing section of said elongated shaft, wherein said second annular ridge has an outer diameter that is larger than the outer diameter of said first annular ridge.

12. The trocar as claimed in claim 1, further comprising:
a flexible wound drain catheter having a first end and a second end;
the first end of said wound drain catheter being secured to said connector, wherein said flexible wound drain catheter has an outer diameter that matches the first diameter of said leading and trailing sections of said elongated shaft;
a drain secured to the second end of said flexible wound drain catheter.

13. A trocar system comprising:
a shaft having a leading section, a trailing section, a reduced diameter midsection located between said leading and trailing sections, and a longitudinal axis extending from a leading end of said leading section to a trailing end of said trailing section of said elongated shaft;
said leading section of said shaft having a tapered region that terminates at a blunt tip located at the leading end thereof, wherein said tapered region includes a sloping surface having a conical shape that tapers away from the longitudinal axis of said elongated shaft and that defines an angle relative to the longitudinal axis of said elongated shaft of about three to five degrees (3-5°);
said trailing section of said shaft having a connector located at the trailing end thereof;
said leading and trailing sections of said shaft having a first diameter and said reduced diameter midsection of said shaft having a second diameter that is smaller than the first diameter for enabling said shaft to be bent at said reduced diameter midsection;
a flexible wound drain catheter having a first end secured to said connector at the trailing end of said trailing section of said shaft, wherein said flexible wound drain catheter has an outer diameter that matches the first diameter of said leading and trailing sections of said shaft.

14. The trocar system as claimed in claim 13, wherein said shaft has a cylindrical shape, and wherein said shaft is made of materials selected from the group consisting of metals, biocompatible metals, medical grade steel, stainless steel, 303 stainless steel, and polymers.

15. The trocar system as claimed in claim 13, further comprising:
said sloping surface of said tapered region and the longitudinal axis of said elongated shaft defining an angle of about three degrees (3°);
said blunt tip including a flat surface, orthogonal to the longitudinal axis, having an outer perimeter and a convexly curved surface surrounding the outer perimeter of said flat surface and extending from the outer perimeter of said flat surface to said sloping surface of said tapered region.

16. A method for draining fluid from a mammal comprising:
attaching a flexible wound drainage catheter to a trocar, said trocar including an elongated shaft having a leading section, a trailing section, a reduced diameter midsection located between said leading and trailing sections, and a longitudinal axis extending from a leading end of said leading section to a trailing end of said trailing section of said elongated shaft, said leading section of said elongated shaft having a tapered region that terminates at a blunt tip located at the leading end thereof, wherein said tapered region of said leading section of said elongated shaft includes a sloping surface having a conical shape that that tapers away from the longitudinal axis of said elongated shaft at an angle of about three to five degrees (3-5°), said trailing section of said elongated shaft having a connector located at the trailing end thereof, said leading and trailing sections of said elongated shaft having a first diameter and said reduced diameter midsection of said elongated shaft having a second diameter that is smaller than the first diameter for enabling said elongated shaft to be bent at said reduced diameter midsection;

bending said trocar to an angulated configuration;

after bending said trocar, passing said trocar through skin of a mammal, wherein said trocar maintains the angulated configuration and said reduced diameter midsection of said elongated shaft is exposed while passing through the skin of the mammal;

passing said trocar out of the skin of the mammal; while maintaining said flexible wound drain catheter within the mammal; and draining fluid from the mammal through said flexible wound drain catheter.

17. The method as claimed in claim 16, wherein said sloping surface of said tapered region and the longitudinal axis of said elongated shaft define an angle of about three degrees (3°), and wherein said blunt tip includes a flat surface having an outer perimeter and a convexly curved surface surrounding the outer perimeter of said flat surface and extending from the outer perimeter of said flat surface to said sloping surface of said tapered region.

18. The method as claimed in claim 16, wherein the first diameter of said leading and trailing sections of said elongated shaft is about 0.125-0.250 inches, and the second diameter of said reduced diameter midsection is about 0.0875-0.0975 inches.

19. The method as claimed in claim 16, wherein said elongated shaft of said trocar has a length of about 6 inches, said leading section of said elongated shaft has a length of about 2.75 inches, said tapered region of said leading section has a length of about 0.741 inches, and said reduced diameter midsection has a length of about 0.400-0.500 inches.

* * * * *